United States Patent [19]

Cooke et al.

[11] Patent Number: 4,684,640
[45] Date of Patent: * Aug. 4, 1987

[54] ANTIBACTERIAL PENEM DERIVATIVES

[75] Inventors: Michael D. Cooke, Newport Pagnell; Barry C. Ross, Luton, both of Great Britain

[73] Assignee: Hoechst Aktiengesellschaft, Frankfurt am Main, Fed. Rep. of Germany

[*] Notice: The portion of the term of this patent subsequent to Apr. 29, 2003 has been disclaimed.

[21] Appl. No.: 718,200

[22] Filed: Apr. 2, 1985

Related U.S. Application Data

[63] Continuation of Ser. No. 395,641, Jul. 6, 1982, abandoned.

[30] Foreign Application Priority Data

Jul. 8, 1981 [GB] United Kingdom ............... 8121107

[51] Int. Cl.$^4$ ................ C07D 499/00; A61K 31/425
[52] U.S. Cl. .................................. 514/195; 514/192; 540/310
[58] Field of Search ............... 260/245.2 R; 514/195, 514/192; 540/310

[56] References Cited

U.S. PATENT DOCUMENTS

| 4,272,437 | 6/1981 | Menard et al. | 260/239 A |
| 4,290,948 | 9/1981 | Brain et al. | 260/245.2 R |
| 4,331,676 | 5/1982 | Gosteli et al. | 260/245.2 R |
| 4,347,183 | 8/1982 | Afonso et al. | 260/245.2 R |
| 4,585,767 | 4/1986 | Cooke et al. | 514/210 |

FOREIGN PATENT DOCUMENTS 0002210 6/1979 European Pat. Off. .
2042515 9/1980 United Kingdom .

Primary Examiner—Nicholas S. Rizzo
Attorney, Agent, or Firm—Curtis, Morris & Safford

[57] ABSTRACT

Penem-derivatives of the formula I

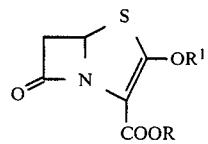

in which
R is hydrogen or a carboxyl esterifying group
$R^1$ is phenyl, naphthyl, thienyl, pyridyl, quinolyl or isoquinolyl any of which is optionally substituted by one, two or three substituents of the group halogen, cycloalkyl, $-NH_2$, $-CONH_2$, $-NO_2$, $-CN$, $-R^2$, $-OR^2$, $-SR^2$, $-SO-R^2$, $-SO_2R^2$, $-CO-R^2$, $-CO-O-R^2$, $-CH_2-CO-O-R^2$, $-NHR^2$, $-NR^2R^{2'}$, $-CO-NH-R^2$, $-CO-NR^2R^{2'}$, $-NH-CO-R^2$, $-NH-CO-NH-R_2$, $-NH-CO-NH-R^2$, $-NH-SO_2-R^2$, $-CF_3$, $-CO-OH$, $-CO_2-CO-OH$ wherein $R^2$ and $R^{2'}$ are the same or different and each represents alkyl of 1 to 4 carbon atoms
or a salts thereof, process for the manufacture thereof and antibacterial pharmaceutical preparations containing them.

14 Claims, No Drawings

ANTIBACTERIAL PENEM DERIVATIVES

This application is a continuation of application Ser. No. 395,641, filed July 6, 1982, now abandoned.

This invention relates to penem derivatives, to a process for their preparation, to pharmaceutical preparations comprising them, and to intermediates for use in the preparation of substances having antibacterial activity and/or β-lactamase inhibitory and/or inactivating activity.

The term "penem" is used herein to denoted the following structure

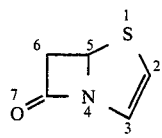

The present invention provides a compound of the general formula I

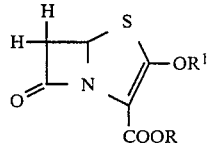

in which
R represents a hydrogen atom or a carboxyl esterifying group, and
$R^1$ represents a phenyl, naphthyl, thienyl, pyridyl, quinolyl or isoquinolyl group bonded at a ring carbon atom to the oxygen atom attached to the 2-position of the penem ring structure, a group $R^1$ being unsubstituted or substituted by one, two or three substituents, which may be the same or different, selected from halogen atoms, cycloalkyl groups having from 5 to 10 carbon atoms, and $-CONH_2$, $-NH_2$, $-NO_2$, $-CN$, $R^2-$, $R^2O-$, $R^2S-$, $R^2-SO-$, $R^2-SO_2-$, $R^2-CO-$, $R^2O-CO-$, $R^2O-CO-CH_2-$,

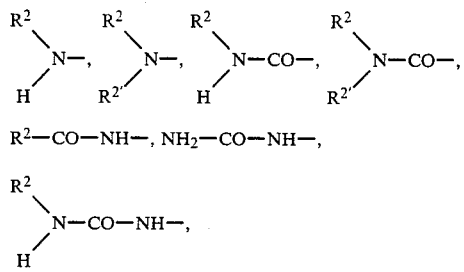

$R^2-SO_2-NH-$, $-CF_3$, $HO-CO-$ and $HO-CO-CH_2$ groups, in which $R^2$ and $R^{2'}$, which may be the same or different, each represents an alkyl group having from 1 to 4 carbon atoms.

The invention also provides salts of a compound of formula I, especially physiologically tolerable salts thereof.

The stereochemistry at position 5 can be R or S, (R and S being as defined by the Cahn-Ingold-Prelog system of nomenclature). The preferred stereochemistry at position 5 is R.

The invention further provides a process for the production of a compound of the general formula I or a salt thereof, which comprises
(i) allowing a compound of the general formula II

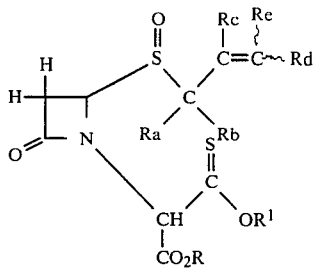

in which R and $R^1$ are as defined above, and Ra, Rb, Rc, Rd and Re, which may be the same or different, each represents a hydrogen atom, or an alkyl group having up to 4 carbon atoms,
and wherein Rc is cis or trans to Rd, to react with a tervalent organophosphorus compound to give a compound of formula I, or
(ii) reacting a compound of the general formula III

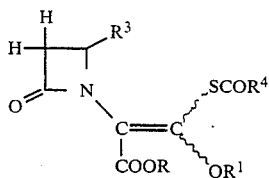

in which
R and $R^1$ are defined above,
$R^3$ represents a chlorine or bromine atom, and
$R^4$ represents an alkyl group having from 1 to 4 carbon atoms, preferably a t-butyl group,
with an aromatic heterocyclic base having a $pK_a$ within the range of from 5 to 9,
and, if desired, carrying out any one or more of the following steps in any desired order:
(a) converting an ester of formula I into the corresponding free acid,
(b) converting a free acid of formula I into an ester thereof,
(c) transesterifying a compound of formula I,
(d) converting a free acid or an ester of formula I into a salt, or a salt into the free acid, an ester, or another salt,
(e) removing any protective groups present other than an esterifying group R,
(f) converting a substituent of a group $R^1$ into another substituent of $R^1$.

The term "lower" as used herein denotes a molecule, group or radical having up to 4 carbon atoms. Unless stated otherwise, halogen atoms are fluorine, chlorine, bromine and iodine atoms. The term "known" means in actual use in the art or described in the literature of the art.

$R^1$ may represent, for example, an unsubstituted phenyl group or a phenyl group substituted by a chlorine, fluorine, trifluoromethyl, methyl, methoxy, nitro, cyano, acetyl, amino, methylthio, methylsulphinyl, methylsulphonyl, methoxycarbonyl, methylcarbonylamino, methylsulphonylamino or methylaminocarbonylmethyl group. $R^1$ may also represent a phenyl group substituted by more than one group, for example by two or three methyl or methoxy groups. A heterocyclic group $R^1$ may also carry up to three substituents, for example, one or two methyl groups, preferably at ring carbon atoms.

It will be appreciated that the choice of substituents for $R^1$ may be subject to considerations of stereochemistry and also of possible interactions between the substituents themselves and other parts of a molecule in which $R^1$ is present, for example, $R^1$ may have 1, 2 or 3 substituents, but not more than one should be selected from (a) —OH and —NH$_2$ groups and not more than one should be selected from (b) —CN, —NO$_2$, $R^3$—CO—, $R^3$O—CO—, $R^3$—SO— and $R^3$—SO$_2$— groups.

(Other substituents may, of couse, be present on $R^1$ in addition to a group selected from (a) and/or a group selected from (b).) The expert will be aware of any restrictions on the choice of substituents, as such restrictions are known in the art.

In a compound of formula II, the group

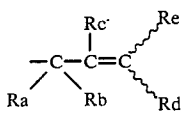

is preferably one of the following:

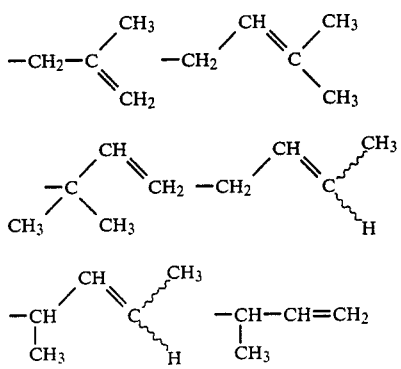

and is especially an unsubstituted allyl group.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms or is, for example a silyl or stannyl ester.

An aliphatic group R is, for example, a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, isobutyl, tert-butyl, n-pentyl, n-hexyl, allyl, or vinyl group.

An aliphatic group R, especially a methyl group, may be substituted by a cycloalkyl, aryl or heterocyclic group, for example, a pyridylmethyl group, or R may itself represent a cycloalkyl, ary or heterocyclic group.

A cycloaliphatic group R may have up to 18 carbon atoms and is, for example, a cyclopentyl, cyclohexyl or adamantyl group. An aryl group R may have up to 12 carbon atoms and may have two or more fused rings. An aryl group R is, for example, an unsubstituted or substituted phenyl group, and an unsubstituted or substituted aralkyl group is, for example, a benzyl, p-nitrobenzyl or benzhydryl group.

A heterocyclic group R may have one or more, preferably one to three, hetero-atoms, which may be the same or different, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms, for example, n-butyl groups, phenyl and benzyl groups, especially three n-butyl groups.

A silyl group R has three substituents on the silicon atom and preferably up to 24 carbon atoms in total. The substituents may be the same or different, and selected from alkyl, alkenyl, cycloalkyl, aryl and aralkyl groups, for example, preferably from alkyl groups having up to 4 carbon atoms, and phenyl groups, and especially from methyl, t-butyl and phenyl groups. Preferred silyl groups are trimethylsilyl, diphenyl-t-butylsilyl, and dimethyl-t-butylsilyl groups.

Any group R that is capable of substitution may be substituted. Examples of substituents are halogen atoms; HO—, $R^2$O—, $R^2$—CO—, $R^2$O—CO—, $R^2$S—CO—, $R^2$—CO—O—, $R^2$—CO—S—, H$_2$N—CO—, H$_2$N—CO—O—,

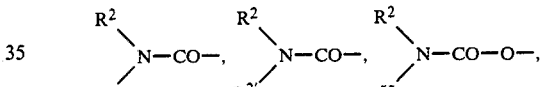

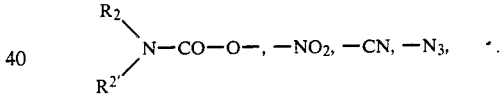

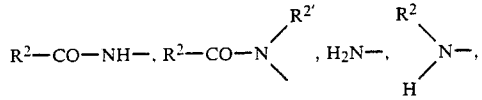

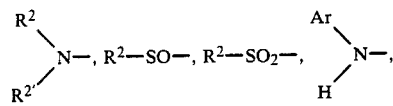

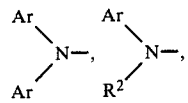

$R^2$—SO$_2$—NH—, Ar, ArO—, ArO—CO—, Ar-S—CO—, Ar—CO—O—, Ar—CO—S—, Ar—R$^2$O—CO—, Ar—R$^2$S—CO—, Ar—R$^2$—CO—O—, Ar—R$^2$—CO—S—, Ar—R$^2$—O—, Ar—R$^2$S—, in which $R^2$ and $R^{2'}$ are as defined above, and Ar denotes an aryl group, especially a phenyl group; aromatic and non-aromatic heterocyclic groups, for example, having one or more heteroatoms, for example, up to 3 hetero atoms, which may be the same or different, selected from nitrogen, oxygen and sulphur atoms, and preferably up to 14 atoms in total, and the corresponding heterocyclicoxy groups and heterocyclicthio groups.

When R represents other than an aliphatic group, a further possible substituent is a lower alkyl group, for example, as defined above.

The group R may be removable by hydrolysis, by photolysis, by reduction or by enzyme action to give the free acid, or two or more methods may be used, for example, reduction followed by hydrolysis. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters. Reduction of an ester, for example, an arylmethyl ester, may be carried out using hydrogen and a metal catalyst, for example, a noble metal, for example, platinum, palladium or rhodium, which catalyst may be supported, for example, on charcoal or kieselguhr.

Alternatively, a p-nitrobenzyl ester may be converted to the free acid by a two-step method, with an initial reduction of the nitro group, followed by hydrolysis. The nitro group may be reduced by noble metal catalysed hydrogenation, for example, using platinum, or palladium on carbon, or by a metal reducing agent, for example, zinc in acetic acid. Other metal reducing agents are, for example, aluminium amalgam, and iron and ammonium chloride, see, for example, British Patent Specification No. 1 582 960. Reduction of the nitro group is followed by hydrolysis which may occur in situ during reduction of the nitro group or which may be carried out subsequently by treatment with an acid or a base. An o-nitrobenzyl ester may be converted to the free acid by photolysis.

A stannyl ester, for example, a tri-n-butyl stannyl ester, may be split readily by hydrolysis, for example, by solvolysis, for example, using water, an alcohol, a phenol or a carboxylic acid, for example, acetic acid.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl ester, e.g. an acetoxymethyl or pivaloyloxymethyl ester, an aminoalkanoyloxymethyl ester, for example, an L-glycyloxymethyl, L-valyloxymethyl or L-leucyloxymethyl ester, or a phthalidyl ester, or an optionally substituted 2-aminoethyl ester, for example, a 2-diethylaminoethyl or 2-(1-morpholino)-ethyl ester.

Preferred esters are the p-nitrobenzyl, phthalidyl, pivaloyloxymethyl, acetylmethyl and acetoxymethyl esters.

An ester of formula I, or of any other free acid described herein, may be prepared by reaction with an alcohol, phenol or stannanol or a reactive derivative thereof. The reaction is preferably carried out under mild conditions in order to prevent rupture of the ring or ring system, for example, under neutral or mild acidic or basic conditions, and at temperatures within the range of from $-70°$ to $+35°$ C.

An alkyl, alkoxyalkyl or aralkyl ester may be prepared by reaction of an acid of formula I or any other free acid with the appropriate diazoalkane or diazoaralkane for example, diazomethane or diphenyldiazomethane. The reaction is preferably carried out in an ether, ester or halogenhydrocarbon as solvent, for example, in diethyl ether, ethyl acetate or dichloromethane. In general, temperatures below room temperature are preferred, for example, from $-15°$ to $+15°$ C.

An ester derived from an alcohol may also be produced by reaction of a reactive derivative of the alcohol, for example, a halide, for example a chloride, bromide or iodide, or a hydrocarbonsulphonyl derivative, for example, a mesyl or tosyl ester, with a salt of an acid of formula I or another free acid described herein for example, an alkali or alkaline earth metal salt, for example, a lithium, sodium, potassium, calcium or barium salt or an amine salt, for example, a triethylammonium salt. This reaction is preferably carried out in a substituted sulphoxide or amide solvent for example, in dimethyl sulphoxide, dimethylformamide or hexamethylphosphoramide or, alternatively, an ester may be prepared by reaction of the acid with the alcohol in the presence of a condensing agent, for example, dicyclohexylcarbodiimide.

A stannyl ester may be formed by reaction of a carboxylic acid of formula I or another free acid described herein, or a salt thereof with a reactive tetravalent tin compound, especially a trialkyl tin oxide.

The present invention also provides the salts of those compounds of formula I that have salt-forming groups, especially the salts of free acids of formula I and the acid addition salts of compounds of formula I having a basic group. The salts are especially physiologically tolerable salts, for example, alkali metal and alkaline earth metal salts, for example, sodium, potassium, lithium, calcium and magnesium salts, ammonium salts and salts with an organic amine; also physiologically tolerable acid addition salts. These may be formed, with suitable inorganic and organic acids, for example, hydrochloric acid, sulphuric acid, organic carboxylic and organic sulphonic acids, for example, trifluoroacetic acid and p-toluenesulphonic acid. Some compounds of formula I which contain a basic centre may exist as Zwitterions; such salts are also part of this invention.

A salt of a free acid of formula I may be produced by reacting the free acid with the appropriate base in a solvent, preferably under conditions under which the salt precipitates. A preferred base is potassium ethylhexanoate.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane, or tetrahydrofuran, in the presence of a metal salt, especially a bicarbonate, for example, in an equivalent amount or in a slight excess, yields a salt directly.

Compounds of the general formula I may be produced in various ways, for example, as shown in the reaction scheme below, in which

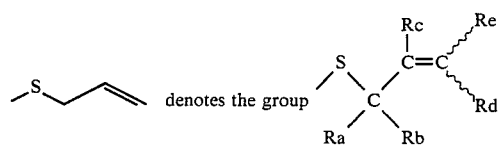

in which Ra to Re are as defined above:

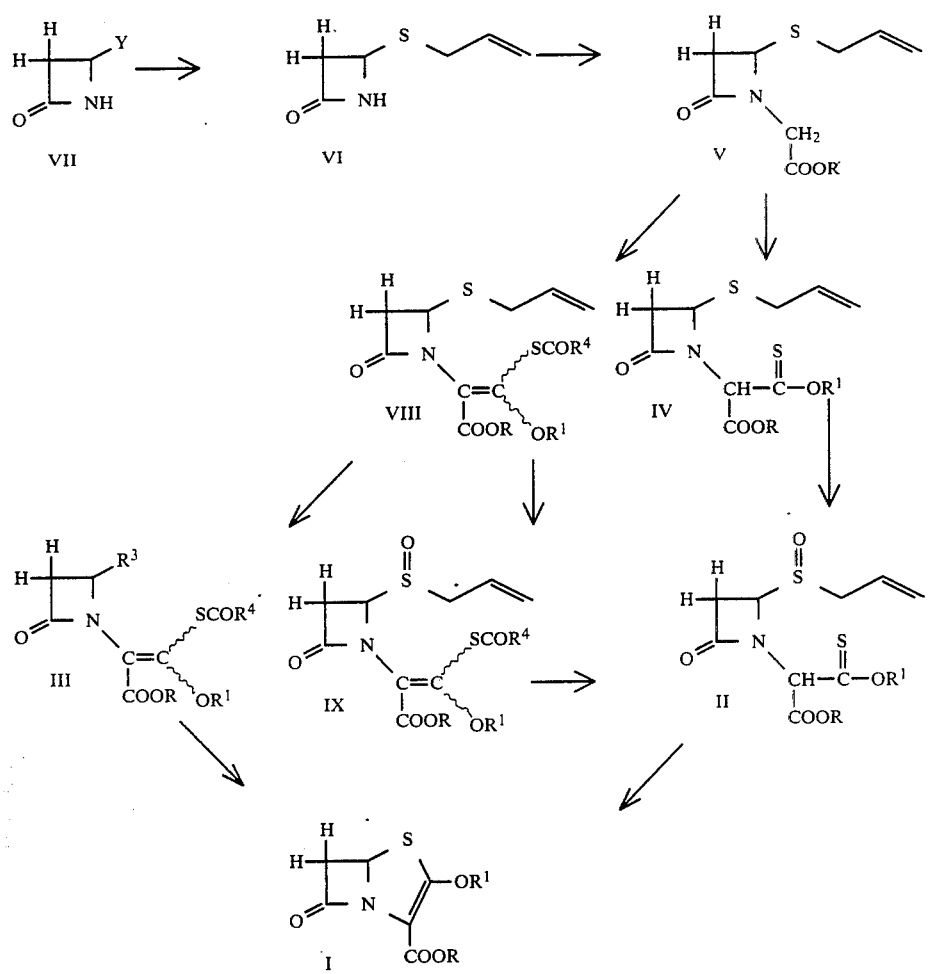

in which R, $R^1$, $R^3$ and $R^4$ are as defined above, and

Y represents a group that is capable of being replaced by a nucleophilic group and is, for example especially an acyloxy or sulphonyloxy group, or a halogen atom. An acyloxy group is, for example, a lower alkylcarbonyloxy group, especially an acetoxy group; a sulphonyloxy group is, for example, a group $-SO_2R^5$ in which $R^5$ represents an alkyl group having from 1 to 4 carbon atoms, or an aryl group, especially a phenyl group; and a halogen atom is especially a chlorine atom.

A compound of formula VII may be prepared as described in Liebigs Annalen Chemie 1974, pp 539–560, Claus, Grimm and Prossel, DT-OS No. 1 906 401, U.K. Specification No. 2 013 674, Japanese Published Application No. 80641, or H. R. Pfaendler, J. Gosteli and R. B. Woodward, J.A.C.S. 102:6, 1980, 2039–2043. A compound of formula VII may be converted into a compound of formula VI by reaction with a compound of formula

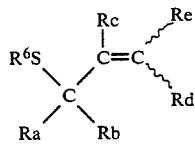

in which $R^6$ represents a hydrogen atom or an alkali metal atom, especially a sodium or potassium atom, and Ra to Re are as defined above.

The reaction is generally carried out in a solvent, preferably a protic solvent, for example, water or an alcohol, or a non-protic, water-miscible solvent which is preferably polar, for example, dimethylformamide, dimethyl sulphoxide, tetrahydrofuran or dioxane. The reaction temperature is, for example, from $-20°$ to $+100°$ C., preferably from $-10°$ to $+20°$ C.

To obtain a compound of formula V, a compound of formula VI may be reacted, in the presence of a base, with a compound of formula X $$Y^1CH_2CO_2R \qquad\qquad X$$

in which
R is as defined above and
$Y^1$ represents a group that is capable of being replaced by a nucleophilic group and is, for example, a halogen atom, preferably a bromine or iodine atom, or a modified hydroxy group, for example, a sulphonyloxy group, for example, a radical of the formula $$-OSO_2R^7$$

in which $R^7$ represents a lower alkyl or $CF_3$ group, or a phenyl group which is unsubstituted or is substituted by a p-nitro, p-bromo, or p-methyl group.

Y[1] preferably represents a bromine or iodine atom or a methylsulphonate, trifluoromethylsulphonate, tolylsulphonate or benzenesulphonate group.

The base may be inorganic, organic or organometallic, for example, an alkali metal or alkaline earth metal hydroxide, oxide, carbonate, bicarbonate or hydride, for example, sodium hydroxide, magnesium oxide, potassium carbonate, potassium bicarbonate or sodium hydride; an amine, for example, a dialkylamine or trialkylamine, for example, triethylamine, DABCO (diazabicyclo(2,2,2)octane), pyridine, or an alkyl-substituted or amino-substituted or dialkylamino-substituted pyridine, for example, N,N-dimethylaminopyridine, or collidine; a guanidine, for example, tetramethylguanidine; DBN (diazabicyclononene) or DBU (diazabicycloundecene); a polymeric base i.e. a base attached to an inert polymeric support, e.g. Hünig's base (diisopropylethylamine attached to e.g. polystyrene); a metallated amine, for example, a metallated alkyl or arylamine, for example, lithium dissopropylamide (LDA), lithium hexamethyldisilazide, lithium piperidide, lithium 2,2,6,6-tetramethylpiperidide, or a Grignard reagent, for example, methylmagnesium bromide. Preferred bases are, for example, potassium carbonate, sodium hydride, lithium diisopropylamide and triethylamine.

The reaction is generally carried out in an aprotic solvent or diluent, for example, a tertiary amide, for example, dimethylformamide, dimethylacetamide or hexamethylphosphoramide; a hydrocarbon, for example, benzene or toluene; or an ether, for example, diethyl ether, tetrahydrofuran or dioxane; a chlorinated hydrocarbon, for example, methylene chloride or chloroform; or acetonitrile, dimethyl sulphoxide, or sulpholane. Dimethylformamide and dimethylacetamide are preferred. A mixture of two or more solvents and/or diluents may be used.

The reaction may be carried out at a temperature within the range of from $-80°$ C. to $+30°$ C., preferably from $-40°$ to $+30°$ C., and especially from $-20°$ to $+20°$ C.

From 1 to 1.5 moles of compound X are preferably used per mole of compound VI, especially from 1 to 1.1 mole of X per mole of VI. The base is used in an amount for example, from 1 to 4 moles of base per mole of compound VI.

The reaction is preferably carried out by dissolving compound VI in a solvent, advantageously in dimethylformamide with stirring, adding the base, adding the compound of formula X and reacting at the desired temperature. The resulting compound of formula V may be worked up and isolated in the usual manner, for example, using chromatographic and/or crystallisation techniques, or the subsequent reaction may be carried out directly on the resulting reaction mixture after removal of any solvent that is not compatible with the subsequent reaction.

If R in formula V represents a carboxyl esterifying group, this group may be converted into another esterifying group R, for example, to introduce a group R that is more easily removable under desired conditions. This transesterification is generally carried out as follows: the ester of formula V is hydrolysed in known manner using, for example, acid or alkaline hydrolysis, preferably using an alkali metal hydroxide, especially sodium or potassium hydroxide. The ester of formula V, for example, a methyl ester, is preferably hydrolysed using an alkali metal hydroxide especially one mole thereof per mole of the ester of formula V in a solvent, for example ethanol, methanol or water, or an aqueous-organic solvent, for example, tetrahydrofuran/water, ethanol/water, or acetonitrile/water.

The reaction mixture may then be acidified to give a solution of pH 1 to 5, preferably 2 to 4, and the free acid may then be isolated and, if desired, the free acid is then esterified with an esterifying agent capable of introducing a different esterifying group R, for example with an alcohol ROH in the presence of an acid or another activating agent, for example, dicyclohexylcarbodiimide, or with an alkylating agent RY[1] in which Y[1] is as defined above. Alternatively, a salt may be isolated and esterified directly. Esterification methods are described above in relation to the compound of formula I.

Transesterification may be carried out on compound V, as described above, or on any other intermediate or on the final product of formula I.

As indicated in the reaction scheme above, compound V may be converted to compound I via compounds IV and II, via compounds VIII, IX and II, or via compounds VIII and III.

A compound of formula V may be converted into a compound of formula IV by reaction, in the presence of a base with a compound of the formula XI

XI in which R[1] is as defined above.

Some compounds of formula XI are known and some are new. New compounds may be prepared by processes analogous to those for the preparation of the known compounds. cf. River & Schalch, Helv. Chem. Acta, Vol 6, 1923, p. 605, and Reich & Martin, Chem Berichte, Vol 98, 1965 p. 2063.

The reaction between compound XI and compound V is carried out in the presence of a base, preferably having a pK $\leq 20$, preferably a metallated amine, and examples of preferred bases are lithium diisopropylamide, lithium hexamethyldisilazide, lithium 6,6,2,2-tetramethylpiperidide, lithium cyclohexyl isopropylamide, and sodamide.

The reaction is generally carried out in an aprotic solvent, for example, an oxygenated hydrocarbon, preferably an ether, for example, diethyl ether, tetrahydrofuran, dioxane, glyme or diglyme. The reaction temperature is, for example, from $-120°$ to $+30°$ C., preferably from $-78°$ to $-20°$ C.

The amount of base used is for example, from 1 to 3 moles, calculated per mole of compound V, preferably from 1.5 to 2.5 moles of base. The thiolating agent of formula XI is preferably used in an amount of from 1 to 1.5 moles per mole of compound V, preferably from 1 to 1.1 moles of compound XI.

The reaction is preferably carried out as follows: to a stirred solution of compound V under an inert atmosphere is added to the base and subsequently a solution of compound XI in the same or a different solvent. To ensure complete reaction between V and XI, the reaction mixture is generally stirred for from 15 to 60 minutes, preferably 30 minutes, and then a proton source is added.

The proton source preferably has a pK of less than 10, and especially from 5 to 2 and is, for example, acetic, citric, oxalic or formic acid.

Oxidation of compound IV may be carried out by any method capable of converting a sulphide into a sulphoxide, for example, there may be used an oxidising agent, for example, hydrogen peroxide, a periodate e.g. sodium periodate, ozone, a peracid e.g. peracetic acid or perbenzoic acid, a substituted perbenzoic acid e.g. m-chloroperbenzoic acid, or a permanganate salt, e.g. potassium permanganate. Preferred oxidising agents are hydrogen peroxide and m-chloroperbenzoic acid. Only 1 equivalent of peracid is generally used per equivalent of compound IV to avoid over-oxidation.

The oxidation is preferably conducted in an inert solvent at a preferred temperature of from $-40°$ to $+30°$. Preferred solvents are ethyl acetate, methylene chloride, chloroform, acetonitrile, and lower alcohols, for example methanol and ethanol.

As indicated above, a compound of formula II may be prepared by another route via compounds VIII and IX. Compound VIII may be prepared from compound V by reaction with a compound of formula XI as described for the production of compound IV, followed by reaction with an activated acid derivative which comprises the group $R^4$, preferably an acid chloride, which has the formula XII

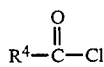

XII in which $R^4$ is as defined above, and is especially a t-butyl group.

After the reaction of compounds V and XI, it is not necessary to add a proton source. The activated acid derivative, preferably of formula XII is preferably added to the mixture resulting from the reaction of compounds V and XI, especially in an amount of from 1 to 2 moles, calculated on compound V. The reaction is preferably carried out at a temperature of from $-80°$ to $+40°$ C., adding the compound of formula XII to the reaction mixture at the temperature at which the reaction between compounds V and XI took place, and then warming, or allowing the mixture to warm, to room temperature, if desired, heating the mixture to a temperature of up to 40° C.

Compound VIII may then be oxidised to give compound IX. Oxidation is preferably carried out as described above for the oxidation of compound IV.

Compound IX may then be converted to compound II by reaction with an aromatic heterocyclic base having a $pK_a$ in the range of from 5 to 9. Imidazole is the preferred base, and the preferred reaction conditions are as described below for the conversion of a compound of formula III into a compound of formula I.

A compound of formula II, which may have been produced by either route, is converted into a compound of formula I by treatment with a tervalent organophosphorus compound, especially of the general formula $PR^8R^9R^{10}$ wherein $R^8$, $R^9$ and $R^{10}$, which may be the same or different, each represents a lower alkyl or lower alkoxy group, a phenyl group or a di-lower alkylamino group. Preferred tervalent organophosphorus compounds are triphenylphosphine, tributylphosphine, trimethylphosphite and triethylphosphite.

The reaction of the compound of formula II with the tervalent organophosphorus compound is preferably carried out under atmospheric pressure in a dry, inert, aprotic organic solvent or diluent, for example, toluene, xylene, glyme, diglyme, dioxane, dimethylformamide or acetonitrile, preferably dioxane or toluene. A mixture of two or more solvents or diluents may be used. The reaction may be carried out at a temperature of from 80° to 140° C., preferably from 100° to 130° C., and it is preferable to use at least 1 equivalent, especially 1.1 equivalents of the phosphorus compound per equivalent of the compound of formula II.

A compound of formula I may be produced by another route from compound V via compounds VIII and III. A method for the production of compound VIII has been described above.

A compound of formula III may be produced by reacting a compound of formula VIII with chlorine, bromine or cyanogen bromide. The halogenation reaction is preferably carried out in a chlorinated hydrocarbon as solvent, generally a chlorinated aliphatic hydrocarbon, and especially dichloromethane or chloroform, and at a temperature of from $-30°$ to $+10°$ C. Generally 1 to 3 moles of chlorine, bromine or cyanogen bromide are used per mole of compound VIII. (cf. S. Kukolja, J. Amer Chem. Soc. (1971) 93 6267, and P. C. Cherry, C. E. Newall and N. S. Watson, J.C.S. Chem. Comm. 1979 p. 663).

A compound of formula III may also be produced by reacting with chlorine, bromine or cyanogen bromide, a compound of formula VIIIa

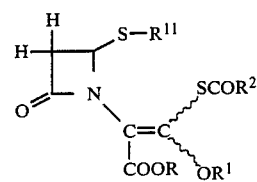

VIIIa in which R, $R^1$ and $R^2$ are defined as above, and $R^{11}$ denotes a phenyl group, or an alkyl group, preferably having up to 8 carbon atoms and especially up to 4 carbon atoms, for example, a t-butyl group. The reaction is carried out as described above for the halogenation of a compound of formula VIII.

A compound of formula VIIIa may be produced by a process analogous to that described above for compound VIII, but from a compound Va, which may be produced from a compound VIa by a process analogous to that described above for the production of compound V. Compounds Va and VIa have the formulae

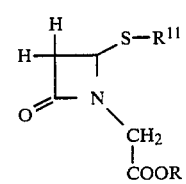

Va

VIa in which R, $R^1$ and $R^{11}$ are defined as above i.e. these compounds are analogues of compounds V and VI, having an alkyl or phenyl group at the sulphur atom instead of an alkenyl group.

A compound of formula VIa may be produced by a process analogous to that described for the production of a compound VI, but using a compound of formula

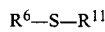

in which $R^6$ and $R^{11}$ are as defined above.

A compound of formula I is produced from a compound of formula III by reaction with an aromatic heterocyclic base having a $pK_a$ within the range of from 5 to 9. Examples of such bases are pyridine and, especially, imidazole. The reaction is generally carried out in a water-miscible solvent containing 5 to 20% (v/v) of water. Examples of water-miscible solvents are tetrahydrofuran, dioxane, acetonitrile, dimethylformamide and nitromethane. A mixture of two or more solvents and water may be used. The reaction temperature is generally within the range of from 0° to 40° C., preferably from 0° to 10° C.

It is advisable to esterify any free carboxyl group present in a compound of formula II or III prior to conversion to a compound of formula I. Although an ester group may be introduced immediately prior to this conversion, it is preferable to esterify the carboxyl group at an earlier stage in the preferred reaction sequence, for example, to esterify a free carboxyl group in a compound of formula IV, V or VIII to ensure that the carboxyl group does not take part in any of the subsequent reactions. An esterifying group may be transesterified to another ester group having more desirable properties for a particular stage of the reaction sequence.

Furthermore, it is advisable to protect any reactive moiety present in any of R or $R^1$ so that such a moiety does not react with any of the reagents used in any subsequent reaction. Examples of moieties which may require protection are hydroxy, carboxy and amine moieties, which may, for example, react with the reagents used to convert compound V to compound VIII. Groups suitable for protecting such reactive moieties are well known, as are methods for their removal. (cf. Protective Groups in Organic Chemistry, editor J. F. W. McOmie, Plenum Press, 1973).

Examples of groups suitable for protecting hydroxyl moieties are tetrahydropyranyl groups, methoxyethoxymethyl groups, acyl groups, for example, acetyl, chloroacetyl and formyl groups, and silyl groups, for example, as described above for R, for example, trimethylsilyl and t-butyldimethylsilyl groups. Carboxy protecting groups are, for example, as described above for R. Amino protecting groups are, for example, t-butyloxycarbonyl, benzyloxycarbonyl, p-nitrobenzyloxycarbonyl, p-nitrobenzenesulphenyl and trityl groups.

Reactive moieites may be protected at any appropriate point in the reaction sequence, and the protective groups are preferably removed after the formation of the compound of formula I, for example, if R in formula I represents an esterifying group, this may be removed in the usual manner, depending on the nature of the ester group, for example, by hydrolysis, reduction, or enzymatically, to yield the free acid. A free acid or an ester may be converted into a salt, especially a physiologically tolerable salt, or a salt may be converted into another salt or the free acid or an ester. An ester may be transesterified, or a free acid converted into an ester, for example, to give an ester capable of removal under physiological conditions. Examples of such proceedures are given above.

The invention also provides a modification of the process described above, wherein in a compound of formula I, II, III, IV, VIII or IX, or in more than one of these compounds a substituent of a group $R^1$ is converted at an appropriate point in the reaction sequence into another substitutent of $R^1$. A substituent of $R^1$ in a compound VIII, for example, may be converted into another substituent before the halogenation reaction to give compound III, or the initial substituent may be retained during the halogenation reaction, being converted into another substituent of $R^1$ before the reaction of compound II to give compound I.

The following are examples of interconversions of substituents of $R^1$:
$R^3S-$ to $R^3SO-$,
$R^3S-$ to $R^3SO_2-$,
$NO_2-$ to $NH_2-$, which may then be alkylated or acylated,
$R^3CO-O-$ to $HO-$, which may then be alkylated or acylated.

The methods for carrying out such reactions are known in the art, for example, an alkylthio group may be oxidised, preferably with a carboxylic peracid, especially m-chloroperbenzoic acid, to give the corresponding alkylsulphinyl or alkylsulphonyl group; a nitro group may be reduced to an amino group by noble metal catalysed hydrogenation, for example, using platinum, or 10% palladium on carbon, cf. M. Freifelder, Catalytic Hydrogenation in Organic Synthsis, Willey Interscience, 1978, page 26, and P. N. Rylander, Catalytic Hydrogenation over Platinum Metals, Academic Press, 1967, Chapter 11; an amino group may be alkylated with a conventional alkylating agent, for example, a lower alkyl halide, for example, methyl iodide, or acylated with, for example, an acid chloride or acid anhydride, for example, acetyl chloride or acetic anhydride.

These modifications of the process of the invention are particularly useful for the production of a compound of formula I having a group $R^1$ bearing 1, 2 or 3 substituents, any one or more of which is potentially unstable during any one or more of the stages of the reaction sequence described above. The conversion step is, accordingly, carried out after the step in which the substituent is potentially unstable.

It will be appreciated that although these modifications are particularly useful for the production of compounds of formula I having substituents on $R^1$ that are potentially unstable in the production process, it is not limited to such groups, and in a further modification of the process of the invention, a substituent of $R^1$ may be produced by conversion of another substituent that does not itself fall within the definition of a substituent of $R^1$, for example, an unsubstituted or substituted, preferably p-nitrosubstituted, benzyloxycarbonylamino group may be converted into a free amino group, for example, by noble metal catalysed hydrogenation, c.f. M. Freifelder, loc. cit., page 111, P. N. Rylander, loc. cit., page 455, and C. Berse et al, J. Org. Chem. 22, 805, 1957.

At each stage of the preferred reaction sequence, the desired compound may be isolated from the reaction mixture and, if desired, purified by appropriate techniques generally used for the purification of organic compounds, for example, chromatography or crystallisation.

As indicated above, various intermediates may be produced in the form of mixture of isomers of various kinds. Such a mixture may be separated or resolved at any stage, or the isomeric mixture may be used per se for subsequent reactions.

All of the compounds that are provided by the invention may exist in any isomeric form, either as a pure isomer or as a mixture of any two or more isomers.

A compound of formula I may have the R- or S-stereochemistry at position 5. Further isomeric forms will occur when any substituent contains a chiral carbon atom. Any mixture of two or more isomeric forms may be resolved if desired, or a compound of formula I can be used in the form of the isomeric mixture. The preferred stereochemistry in compound I at position 5 is generally R, corresponding to that of the naturally occurring penicillins and cephalosporins.

The compounds of formula I and salts thereof are $\beta$-lactamase inhibitors, and the compounds are generally stable to the action of $\beta$-lactamases produced by gram-positive organisms, for example, by *Staphylococcus aureus* and gram negative organisms, for example, Enterobactercloacae. They also possess antibacterial properties themselves and may be used in humans and other animals, for example, to treat bacterial infections caused by gram positive and gram negative bacteria, for example, *Staphylococcus aureus, Streptococcus pyogenes, Bacillus subtilis, E. coli, Pseudomonas aeruginosa,* and *Proteus inorganii,* some strains of which are penicillin-resistant.

The invention accordingly provides a pharmaceutical preparation which comprises a compound of formula I, or a physiologically tolerable salt thereof, or a mixture of two or more such substances as active ingredient, in admixture or conjunction with a pharmaceutically suitable carrier. The preparation may also comprise one or more other pharmaceutically active substances, for example, another antibacterial substance, especially one which has a $\beta$-lactam ring. The preparations may be in a form suitable for enteral or parenteral administration, for example, for oral, intravenous, or intramuscular administration, for example, as tablets, capsules, syrups, or sterile injectable or infusible solutions. The preparations are advantageously in unit dosage form and preferably comprise from 10 to 2000 mg of the active ingredient. The daily dosage of the active ingredient is generally from 20 to 8000 mg, in divided doses, generally up to 4 doses.

The invention also provides the use of an active ingredient as defined above as a $\beta$-lactamase inhibitor and/or as an antibacterial agent.

The invention further provides a pharmaceutical preparation which comprises a compound of formula I, or a physiologically tolerable salt thereof, or a mixture of two or more such substances, in unit dosage form.

The invention also provides a pharmaceutical preparation which comprises a compound of formula I or a physiologically tolerable salt thereof or a mixture of two or more such substances, and one or more further pharmaceutically active substances, for example, as described above and, for example, in unit dosage form.

Unit dosages are preferably as described above.

The following Table provides examples of compounds of the invention.

TABLE

| R | R¹ | R | R¹ |
|---|---|---|---|
| H | phenyl | H | 2,5-dimethylthiophen-3-yl |
| H | 4-chlorophenyl | H | pyridin-3-yl |
| H | 4-fluorophenyl | H | 2,6-dimethylpyridin-3-yl |
| H | 4-methylphenyl | H | 4-acetamidophenyl |
| H | 4-methoxyphenyl | H | 4-aminophenyl |

TABLE-continued

Structure:

4-H azetidinone with S-substituent: β-lactam ring bearing H at C-3 and S-C(=CH-OR¹)(CO₂R) side chain at N.

| R | R¹ | R | R¹ |
|---|---|---|---|
| H | 4-(CF₃)-phenyl | H | 2-thienyl |
| H | 4-NO₂-phenyl | H | 4-(SCH₃)-phenyl |
| H | 2,4,5-tri(OCH₃)-phenyl | H | 4-(S(=O)CH₃)-phenyl |
| | | H | 4-CN-phenyl |
| H | 4-(C(=O)OCH₃)-phenyl | H | 4-(NH—SO₂—CH₃)-phenyl |
| H | 4-(NH—CO—NH—CH₃)-phenyl | H | 4-(SO₂—CH₃)-phenyl |

Alternatively, for each of the above groups $R^1$, R may represent $Na^+$, $K^+$, $Li^+$, or a pivaloyloxymethyl or phthalidyl group.

The stereochemistry at position 5 is preferably R.

The present invention also provides compounds of the general formulae II, III, IV, V, Va, VI, VIa, VIII, VIIIa and IX and more especially provides the compounds specifically described in the Table and Examples given hereinafter.

The following Examples illustrate the invention. In them, temperatures are expressed in degrees Celsius, and T.L.C. denotes thin layer chromatography.

EXAMPLE 1

4-Allylthioazetidin-2-one

A solution of 42.9 g of sodium hydroxide in 500 ml of water was made up under nitrogen and cooled to room temperature, 108 ml of allyl mercaptan was added and the mixture stirred under nitrogen for 30 minutes. 138.7 g of 4-acetoxyazetidin-2-one was added to the mixture over 10 minutes under nitrogen and the reaction mixture was stirred overnight in an air atmosphere. The reaction mixture was extracted into dichloromethane (6×250 ml). The organic layer was washed with water (2×250 ml), dried over magnesium sulphate and evaporated in vacuo to dryness. Purification, over silica gel and elution with hexane-ethylacetate, afforded the above product as a yellow oil. (112.1 g, 73% of the theoretical yield).

$\nu$max=1769, 1778 (sh) cm$^{-1}$.

δ(CDCl₃): 2.86 (1H, ddd, $J_{NH,3}$ 1.5 Hz, $J_{4,3}$ 3 Hz, $J_{3\alpha,3\beta}$ 15 Hz, 3β-H), 3.28 (2H, d, J 7 Hz, S—CH₂), 3.37 (1H, ddd, $J_{NH,3}$ 1.5 Hz, $J_{4,3}$ 6 Hz, $J_{3\beta,3\alpha}$ 15 Hz, 6α-H), 4.71 (1H, dd, $J_{trans}$ 3 Hz, $J_{cis}$ 6 Hz, 4-H), 4.93–5.38 (2H, m, =CH₂), 5.49–6.24 (1H, m, CH=), 7.43 (1H, bs, NH).

m/e 143.0405 (M+).

EXAMPLE 2

4-Nitrobenzyl 2-(4-allylthioazetidin-2-on-1-yl)acetate 11.5 g of 4-nitrobenzylbromoacetate in 30 ml of dimethylformamide was added to 5.0 g of 4-allylthioazetidin-2-one dissolved in 70 ml of dimethylformamide with stirring under argon at room temperature. After 5 mins, 10.61 g of potassium carbonate was added to the solution. During the following 20 mins there was a colour change in the mixture from yellow to dark brown. Stirring was continued for a further 3 hours 40 mins. The mixture was then poured into water (300 ml), extracted into ethyl acetate (4×100 ml) and the combined organic extracts washed with water (3×200 ml). The organic layer was dried with MgSO₄ and evaporated to leave a yellow oil.

The crude product was chromatographed on silica gel using ethylacetate/hexane mixtures as eluent. 5.89 g of product was obtained (50% of the theoretical yield).

δ(CDCl$_3$): 3.05(1H, 2d, J trans 3 Hz, 3—H), 3.17(1H, S, S—CH$_2$—), 3.30(1H, S, S—CH$_2$—), 3.53(1H, 2d, J cis, 5 Hz, J gem 15 Hz, 3—H), 3.84 and 4.38 (2H, ABq, J 18 Hz, —N—CH$_2$—), 4.95 (1H, 2d, 4—H), 5.00-5.34(2H, m, =CH$_2$), 5.34(2H, S, —O—CH$_2$), 5.54-6.40(1H, m, =CH), 7.53-8.38(4H, m, —C$_6$H$_4$).

νmax (CDCl$_3$)=1769, 1758 cm$^{-1}$.

m/e 336.0525 (M+), 295.0391 (M—CH$_2$CHCH$_2$), 136.0385 (base peak).

EXAMPLE 3

Methyl 2-(4-allylthioazetidin-2-on-1-yl)acetate 21.8 ml of methyl bromoacetate in 220 ml of dimethylformamide was added to 31.1 g of 4-allylthioazetidin-2-one dissolved in 420 ml of dimethylformamide, with stirring, under argon, at room temperature. After 5 mins, 66.0 g of anhydrous potassium carbonate was added to the solution. The suspension was then stirred for a further 18 hours.

The mixture was poured into water (2.5 l), extracted into ethyl acetate (3×1200 ml) and washed with water (3×2 l). The organic layer was dried with MgSO$_4$ and evaporated to leave a yellow oil.

The crude product was chromatographed on silica gel using ethyl acetate/hexane mixtures as eluent, 22.0 g of the above product was obtained. (47% of the theoretical yield).

δ(CDCl$_3$): 2.97 (1H, 2d, J trans 3 Hz, 3—H), 3.16(1H, S, S—CH$_2$—), 3.26 (1H, S, S—CH$_2$—), 3.45 (1H, 2d, J cis 5 Hz, J gem 15 Hz, 3—H), 3.66 and 4.23(2H, ABq, J 17 Hz, —N—CH$_2$—), 3.72 (3H, S, CH$_3$), 4.86(1H, 2d, 4—H), 5.95-5.27(2H, m, =CH$_2$), 5.50-6.15 (1H, m, =CH).

νmax (CHCl$_3$)=1766, 1749 cm$^{-1}$.

m/e 215.0539(M+): 142.0456 (base peak).

EXAMPLE 4

Methyl 2-(4-allylthioazetidin-2-on-1-yl)acetate 0.070 ml of methylbromoacetate in 1 ml of dimethylformamide was added to 0.100 g of 4-allylthioazetidin-2-one dissolved in 2 ml of dimethylformamide with stirring under argon at 0°. After 5 mins, 0.040 g of hexane-washed sodium hydride, was added to the solution. The cooling bath was removed and stirring continued for a further 45 minutes.

The mixture was poured into water (15 ml), extracted into ethyl acetate (2×12 ml) and washed with water (3×15 ml). The organic layer was dried with MgSO$_4$ and evaporated to leave a yellow oil. Yield: 0.089 g, (59% of the theoretical yield). (For spectral data see Example 3).

EXAMPLE 5

2-(4-Allylthioazetidin-2-on-1-yl)acetic acid 2.34 g of potassium hydroxide dissolved in a mixture of 285 ml of ethanol and 15 ml of water was added to 6.0 g of methyl 2-(4-allylthioazetidin-2-on-1-yl)acetate with stirring at room temperature. The solution was poured into 720 ml 1M hydrochloric acid, extracted into dichloromethane (2×650 ml), the organic layer extracted with saturated sodium bicarbonate solution and the aqueous phase acidified to pH 1 with 5M hydrochloric acid. This solution was extracted into dichloromethane (5×650 ml), dried with MgSO$_4$ and evaporated to leave a colourless oil. Yield: 5.37 g (96%).

δ(CDCl$_3$): 3.06(1H, 2d, J trans 3 Hz, 3—H), 3.19(1H, S, S—CH$_2$—), 3.30(1H, S, S—CH$_2$), 3.53(1H, 2d, J cis 5 Hz, J gem 16 Hz, 3—H), 3.75 and 4.36(2H, ABq, J 18 Hz, N—CH$_2$—), 4.96(1H, 2d, 4—H), 5.03-5.34(2H, m, =CH$_2$), 5.58-6.26(1H, m, H—CH=).

νmax (CDCl$_3$)=1765, 1730 cm$^{-1}$.

m/e 201.0500 (M+), 86.0239 (base peak).

EXAMPLE 6

Pivaloyloxymethyl 2-(4-allylthioazetidin-2-on-1-yl)-2-carboxylate

To a solution of 14 mls of diisopropylamine and 20.4 g of 2-(4-allylthioazetidin-2-on-1-yl)carboxylic acid in 450 ml of dimethylformamide, at 0° C., was added dropwise 14 ml of chloromethylpivalate. The solution was warmed to room temperature and stirred for 5 days. The reaction mixture was then poured into water (500 ml), and extracted into ethyl acetate (3×500 ml); the organic layer was washed with hydrochloric acid (pH 2.0, 400 ml), then water (2×500 ml), dried over magnesium sulphate and evaporated to dryness. The crude product was purified over silica gel eluting with hexane ethyl acetate to give the above product as a pale yellow oil (20.1 g, 63%).

ν$_{max}$=1760, 1768, 1776 cm$^{-1}$.

δ(CDCl$_3$): 1.20 (9H, s, C(CH$_3$)$_3$), 2.99 (1H, dd, J$_{trans}$ 3 Hz, J$_{3\alpha,3\beta}$ 16 Hz, 3β—H), 3.27(2H, d, J 7 Hz, S—CH$_2$), 3.53 (1H, dd, J$_{cis}$ 5 Hz, J$_{3\beta,3\alpha}$ 16 Hz, 3α—H), 4.08 (2H, q, J 18 Hz, N—OH$_2$), 4.93 (1H, dd, J$_{cis}$ 5 Hz, J$_{trans}$ 3 Hz, 4-H), 5.03-5.50 (2H, m, =CH$_2$), 5.57-6.23 (1H, m, CH=), 6.80(2H, 3, CO$_2$CH$_2$).

EXAMPLE 7

4-Nitrobenzyl 2-(4-allythioazetidin-2-on-1-yl)-3-thioxo-3-(4-tolyloxy)-propionate To a stirred solution of 10 g of 4-nitrobenzyl 2-(4-allylthioazetidin-2-on-1-yl)-2-acetate in 150 ml of THF at −78° under argon was added a solution of a mixture of 14 ml of hexamethyldisilazane and 67.2 mmol of n-butyllithium in 100 ml of dry THF.

The mixture was stirred for 30 minutes and a solution of 5.55 g of p-tolyloxychlorothionoformate in 20 ml of THF was added, the mixture was warmed to −40° C. over a 30 minute period and quenched with 5 ml of acetic acid. The mixture was evaporated in vacuo to dryness; the resulting oil was portioned between ethyl acetate and water, the organic layer was separated and washed with water, saturated sodium bicarbonate and brine; it was then dried over MgSO$_4$ and evaporated to dryness. Chromatography on silica gel afforded 8.27 g of the title product as a yellow oil (57% of the theoretical yield).

λ$_{max}$=1770, 1757 (sh) cm$^{-1}$.

δ(CDCl$_3$): 2.34 (3H, s, —CH$_3$), 3.10 (1H, 2d, J$_{trans}$ 3 Hz, J$_{3\alpha,3\beta}$ 16 Hz, 3β—H), 3.28 (2H, d, J 7 Hz, S—CH$_2$), 3.54 (1H, 2d, J$_{cis}$ 6 Hz, J$_{3\beta,3\alpha}$ 16 Hz, 3α—H), 4.98 (1H, dd, J$_{cis}$ 6 Hz, J$_{trans}$ 3 Hz, 4—H), 5.07-5.31 (2H, m, CH$_2$=), 5.37 (2H, s, CO$_2$CH$_2$), 5.41 (1H, s, HCCO$_2$), 5.40-6.12 (1H, m, CH=), 6.79-7.17 (4H, m, 7.43–8.28 (4H, m, O—C6H4—CH3), (—C6H4—NO2).

m/e base peak 108.0572.

EXAMPLE 8

4-Nitrobenzyl 2-(4-allylsulphinylazetidin-2-on-1-yl)-3-thioxo-3-(4-tolyloxy)propionate To a stirred solution of 304 mg of 4-nitrobenzyl 2-(4-allylthioazetidin-2-on-1-yl)-3-thioxo-3-(4-tolyloxy)propionate in ethyl acetate at −20° was added a solution of 155 mg of m-chloroperoxybenzoic acid in ethyl acetate over 10 minutes.

After 30 minutes, the reaction mixture was washed with saturated sodium bicarbonate solution, dried over MgSO4 and evaporated in vacuo to dryness. Chromatography over silica gel afforded 120 mg of the title product as a yellow oil (62% yield).

$v_{max} = 1785$ cm$^{-1}$.

$\beta$(CDCl3): 2.35 (3H, s, —CH3), 3.06 (1H, 2d, J$_{trans}$ 3 Hz, J$_{3\alpha,3\beta}$16 Hz, 3$\beta$—H), 3.37 (2H, d, J 7 Hz, —CH2—), 3.62 (1H, 2d, J$_{cis}$ 6 Hz, J$_{3\beta,3\alpha}$16Hz, 3$\alpha$—H), 5.20 (1H, dd, J$_{trans}$ 3 Hz, J$_{cis}$ 6 Hz, 4—H), 5.25–5.50 (2H, m, CH2=), 5.39 (2H, s, CO2—CH2), 5.51 (1H, s, HCCO2), 5.57–6.26 (1H, m, CH=), 6.77–7.33 (4H, m,

O—C6H4—CH3), 7.48–8.28 (4H, m,

—C6H4—NO2).

mass spec.: base peak 57.0376

O—CH2—CH=CH2

EXAMPLE 9

4-Nitrobenzyl 7-oxo-3-(4-tolyloxy)-4-thia-1-azabicyclo[3,2,0]hept-2-ene-2-carboxylate To a stirred solution of 59 mg of 4-nitrobenzyl 2-(4-allylsulphinylazetidin-2-on-1-yl)-3-thioxo-3-(4-tolyloxy)propionate in 2ml of dry dioxan under nitrogen was added a solution of 30 mg of triphenylphosphine in 1 ml of dry dioxan. The mixture was heated under reflux for 15 minutes, and the mixture was then evaporated in vacuo to dryness. Chromatography over silica gel, eluting with hexane/ethyl acetate mixtures, afforded 10 mg of the penem product as a yellow oil. (21% yield).

$v_{max} = 1798$ cm$^{-1}$.

$\delta$(CDCl3): 2.38 (3H, s, —CH3), 3.46 (1H, 2d, J$_{trans}$ 1.5 Hz, J$_{6\alpha,6\beta}$16 Hz, 6$\beta$—H), 3.91 (1H, 2d, J$_{cis}$ 3 Hz, J$_{6\beta,6\alpha}$16 Hz, 6$\alpha$—H), 5.37 (2H, m, CO2CH2—), 5.66 (1H, dd, J$_{trans}$ 1.5 Hz, J$_{cis}$ 3 Hz, 5-H), 7.11 (4H, s,

O—C6H4—), 7.48–8.25 (4H, m,

—C6H4—NO2).

mass spec.: molecular ion 412.067, base peak 136.041

—CH2—C6H4—NO2.

EXAMPLE 10

Sodium 7-oxo-3-(4-tolyloxy)-4-thia-1-azabicyclo[3,2,0]hept-2-ene-2-carboxylate

To a solution of 53 mg of 4-nitrobenzyl 7-oxo-3-(4-tolyloxy)-4-thia-1-azabicyclo[3,2,0]hept-2-ene-2-carboxylate in dioxan was added an aqueous solution of 10 mg of sodium bicarbonate, and 50 mg of palladium on charcoal (10%). The mixture was hydrogenated with shaking at 50 p.s.i. for 90 minutes.

The mixture was then filtered through Celite, and lyophilised to afford the title compound as a yellow powder (35 mg).

$\delta$(D2O): 2.42 (3H, s, CH3), 3.50 (1H, dd, J$_{trans}$ 1.5 Hz, J$_{gem}$ 16 Hz, 6—H), 3.98 (1H, dd, J$_{cis}$ 3 Hz, J$_{gem}$ 16 Hz, 6—H), 5.75 (1H, dd, J$_{cis}$ 3 Hz, J$_{trans}$ 1.5 Hz, 5—H), 7.22 (4H, s, p—C6H4).

EXAMPLE 11

7-Oxo-3-(4-tolyloxy)-4-thia-1-azabicyclo[3,2,0]hept-2-ene-2-carboxylic acid

An aqueous solution of 32 mg of sodium 7-oxo-3-(4-tolyloxy)-4-thia-1-azabicyclo[3,2,0]hept-2-ene-2-carboxylate was acidified to pH 2.0 with dilute hydrochloric acid, and was then extracted with ethyl acetate. The organic layer was backwashed with water, and then dried and evaporated in vacuo to afford 14.3 mg of the above acid as a solid.

$v_{max}$ (CDCl3) = 1778 cm$^{-1}$.

EXAMPLE 12

4-Nitrobenzyl 2-(4-allythioazetidin-2-on-1-yl)-3-phenoxy-3-thioxo-propionate To a stirred solution of 3.28 g of 4-nitrobenzyl-2-(4-allylthioazetidin-2-on-1-yl)-2-acetate in 50 ml of dry THF at −78° under argon was added a solution of a mixture of 4.6 ml of hexamethyldisilazane and 9.74 mmol of n-butyllithium in 25 ml of dry THF. The mixture was stirred for 30 minutes and a solution of 1.68 g of phenyl chlorothionoformate in 10 ml of dry THF was added; the mixture was warmed to −40° over a 30 minute period and quenched with 2 ml of acetic acid. The mixture was evaporated in vacuo to dryness; the resulting oil was partitioned between ethyl acetate and water, the organic layer was separated and washed with water, saturated sodium bicarbonate and brine, was dried over MgSO$_4$ and evaporated to dryness. Chromatography on silica gel afforded 3.19 g of the title compound as a yellow oil (69% of the theoretical yield).

$\nu_{max} = 1770$ cm$^{-1}$.

δ(CDCl$_3$): 3.10 (1H, 2d, J$_{trans}$ 3 Hz, J$_{3\alpha,3\beta}$16 Hz, 3β—H), 3.28 (2H, d, J 7 Hz, S—CH$_2$), 3.55 (1H, 2d, J$_{cis}$ 5 Hz, J$_{3\alpha,3\beta}$16 Hz, 3α—H), 4.98–6.5 (7H, m, 4—H, CH=CH$_2$, HCCO$_2$, CO$_2$CH$_2$), 6.8–7.8 (5H, m, C$_6$H$_5$), 7.5–8.4 (4H, m,

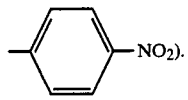

).

EXAMPLE 13

4-Nitrobenzyl 2-(4-allylsulphinylazetidin-2-on-1-yl)-3-phenoxy-3-thioxopropionate To a stirred solution of 3.62 g of 4-nitrobenzyl 2-(4-allythioazetidin-2-on-1-yl)-3-phenoxy-3-thioxopropionate in ethyl acetate at −20° was added a solution of 1.65 g of 80% m-chloroperoxybenzoic acid in ethyl acetate over 10 minutes. The reaction mixture was washed with saturated sodium bicarbonate solution, dried over MgSO$_4$, and evaporated in vacuo to dryness. Chromatography over silica gel afforded the title compound as a yellow oil.

$\nu_{max} = 1787$ cm$^{-1}$.

δ(CDCl$_3$): 3.0–3.8 (4H, m, SCH$_2$,

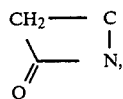

5.1–6.3 (7H, m, —CH=CH$_2$, 4—H, CHCO$_2$,

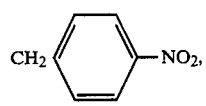

6.9–8.4 (9H, m, C$_6$H$_5$ and

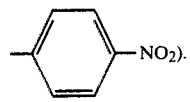

).

EXAMPLE 14

4-Nitrobenzyl 7-oxo-3-phenoxy-4-thia-1-azabicyclo[3,2,0]hept-2-ene-2-carboxylate A stirred solution of 97 mg of 4-nitrobenzyl 2-(4-allylsulphinylazetidin-2-on-1-yl)-3-phenoxy-3-thioxopropionate and 52 mg of triphenylphosphine in 2 ml of dry dioxan was heated under an argon atmosphere under reflux for 15 minutes. The mixture was then evaporated in vacuo to dryness; chromatography over silica gel afforded 14 mg of the title compound (18% theoretical yield).

$\nu_{max} = 1794$ cm$^{-1}$.

δ(CDCl$_3$): 3.43 (1H, 2d, J$_{trans}$ 1.8 Hz, J$_{6\alpha,6\beta}$16 Hz, 6β—H), 3.87 (1H, 2d, J$_{cis}$ 3.4 Hz, J$_{6\alpha,6\beta}$16 Hz, 6α—H), 5.33 (2H, m, CO$_2$CH$_2$—), 5.65 (1H, 2d, J$_{cis}$ 3.4 Hz, J$_{trans}$ 1.8 Hz, 5—H), 7.0–7.5 (5H, m, —C$_6$H$_5$), 7.4–8.3 (4H, m,

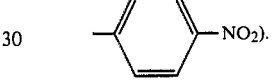

).

EXAMPLE 15

Sodium 7-oxo-3-phenoxy-4-thia-1-azabicyclo[3,2,0]hept-2-ene-2-carboxylate

A mixture of a solution of 56 mg of 4-nitrobenzyl-7-oxo-3-phenoxy-4-thia-1-azabicyclo[3,2,0]hept-2-ene-2-carboxylate in 3 ml of dioxan and 12.5 mg of sodium bicarbonate in 2 ml of water, and 10% palladium/charcoal was hydrogenated at 50 psi at 25° for 90 minutes. The mixture was then filtered through Celite, and lyophilized to yield 30 mg of the title compound as a pale yellow crystalline solid.

EXAMPLE 16

4-Nitrobenzyl 2-(4-allylthioazetidin-2-on-1-yl)-3-phenoxy-3-trimethylacetylthio-propenate To a stirred solution of 2.94 g of 4-nitrobenzyl 2-(4-allylthioazetidin-2-on-1-yl)-2-acetate in 50 ml of dry THF at −78° under argon was added a solution of a mixture of 4.15 ml of hexamethyldisilazane and 19.7 mmol of n-butyllithium in 15 ml of dry THF. The mixture was stirred for 5 minutes, and a solution of 1.51 g of phenyl chlorothionoformate in 10 ml of dry THF was added. The mixture was warmed to −35°, and after 5 minutes was then cooled to −78°, and a solution of 1.26 g of pivaloyl chloride in 10 ml dry THF was added. The mixture was warmed to room temperature and, after 30 minutes, the mixture was evaporated in vacuo, and then chromatographed on silica gel. Elution with ethyl acetate-hexane mixtures afforded the title compound as a deep orange oil.

δ(CDCl$_3$): 1.03 and 1.07 (9H, S, C(CH$_3$)$_3$), 3.0–3.5 (4H, m, SCH$_2$ and 3—H), 5.00 (1H, dd J$_{trans}$ 2 Hz J$_{cis}$ 4

Hz, 4—H), 5.1–6.5 (5H, m, CH$_2$, CH=CH$_2$), 6.9–8.35 (9H, m, C$_6$H$_5$ and

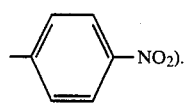

EXAMPLE 17

4-Nitrobenzyl 2-(4-allylsulphinylazetidin-2-on-1-yl)-3-phenoxy-3-trimethylacetylthio-propenate To a solution of 3.4 g of 4-nitrobenzyl 2-(4-allylthioazetidin-2-on-1-yl)-3-phenoxy-3-trimethylacetylthiopropenate in ethyl acetate at −20° C. was added a solution of 1.32 g of 80% m-chloroperoxybenzoic acid in 10 ml of ethyl acetate over 10 minutes. The reaction mixture was washed with saturated sodium bicarbonate solution, dried over MgSO$_4$, and evaporated in vacuo to dryness. Chromatography over silica gel and elution with ethyl acetate-hexane mixtures afforded 2.36 g of the title compound as a yellow oil (67% of the theoretical yield).

$\nu_{max}$ (CDCl$_3$) = 1785 cm$^{-1}$.

δ(CDCl$_3$): 1.01 and 1.05 (9H, 2s, C(CH$_3$)$_3$), 3.15–3.8 (4H, m, SCH$_3$ and 3—H), 5.0–6.0 (6H, m, CH=CH$_2$, 4—H and OCH$_3$), 6.9–8.32 (9H, m, C$_6$H$_5$ and C$_6$H$_4$NO$_2$).

EXAMPLE 18

4-Nitrobenzyl 2-(4-allylsulphinylazetidin-2-on-1-yl)-3-phenoxy-3-thioxo-propanate To a stirred solution of 0.53 g of 4-nitrobenzyl 2-(4-allylsulphinylazetidin-2-on-1-yl)-3-phenoxy-3-trimethylacetylthio-propenate in dioxan-water (9:1 v/v) at room temperature was added 84 mg of imidazole. After 30 minutes, the mixture was partitioned between ethyl acetate and water. The organic layer was separated, and was washed with water, with aqueous citric acid, with water, with saturated sodium bicarbonate, and with brine, was dried over MgSO$_4$, and then evaporated in vacuo to dryness. Chromatography over silica gel and elution with ethyl acetate-hexane mixtures afforded 517 mg of the title compound (contaminated with pivalic acid) as a yellow oil.

EXAMPLE 19

4-Nitrobenzyl 7-oxo-3-phenoxy-4-thia-1-azabicyclo[3,2,0]hept-2-ene-2-carboxylate A mixture of 1550 mg of 4-nitrobenzyl 2-(4-allylsulphinylazetidin-2-on-1-yl)-3-phenoxy-3-thioxo-propanate (containing 10% pivalic acid), 808 mg of triphenylphosphine and dioxan was heated under an argon atmosphere at 110° C. for 15 minutes. The mixture was evaporated in vacuo to dryness, and the resulting oil was chromatographed on silica gel. Elution with ethyl acetate-hexane mixtures afforded 219 mg of a solid. This was taken up in ethyl acetate and extracted with sodium bicarbonate to afford, after evaporation in vacuo, 192 mg of the title compound (11% of the theoretical yield).

EXAMPLE 20

4-Nitrobenzyl 2-(4-allylthioazetidin-2-on-1-yl)-3-(4-methoxyphenoxy)-3-trimethylacetylthiopropenate To a stirred solution of 2.0 g of 4-nitrobenzyl 2-(4-allylthioazetidin-2-on-1-yl)-acetate in dry THF at −78° C. under argon was added a solution of a mixture of 2.8 ml of hexamethyldisilazane and 13.4 mmol of n-butyllithium in dry THF. The mixture was stirred for 30 minutes, and a solution of 0.92 ml of 4-methoxyphenyl chlorothionoformate in 7 ml of dry THF was added. The mixture was warmed to −40° C., and after 30 minutes was then cooled to −78°, and a solution of 0.8 ml of pivaloyl chloride in dry THF was added. The mixture was warmed to room temperature, and, after 30 minutes, the mixture was evaporated in vacuo to dryness. The resulting oil was partitioned between ethyl acetate and water, the organic layer was separated, and was washed with water, with aqueous citric acid, with saturated sodium bicarbonate, with brine, and was then dried over MgSO$_4$ and evaporated to dryness. Chromatography over silica gel, eluting with hexane-ethyl acetate mixtures afforded the title compound (2.3 g, 60%) as a yellow oil.

$\nu_{max}$ (CDCl$_3$) = 1769 cm$^{-1}$.

δ(CDCl$_3$): 1.05–1.10 (9H, 2s, (CH$_3$)$_3$), 3.1–3.5 (4H, m, S—CH$_2$, 3—H), 3.80 (3H, s, OCH$_3$), 5.00 (1H, dd, J$_{trans}$1.5 Hz, J$_{cis}$ 3 Hz, 4—H), 5.15–5.48 (4H, m, CH$_2$=, CO$_2$CH$_2$), 5.50–6.20 (1H, m, CH=), 6.7–8.4 (8H, m,

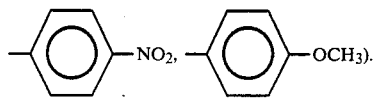

EXAMPLE 21

4-Nitrobenzyl 2-(4-allylsulphinylazetidin-2-on-1-yl)-3-(4-methoxyphenoxy)-3-trimethylacetylthio-propenate To a solution of 0.35 g of 4-nitrobenzyl 2-(4-allylthioazetidin-2-on-1-yl)-3-(4-methoxyphenoxy)-3-trimethylacetylthio-propenate in ethyl acetate at −78° C. was added a solution of 0.128 g of 80% m-chloroperoxybenzoic acid in ethyl acetate over 10 minutes. The reaction mixture was washed with saturated sodium bicarbonate solution, was dried over MgSO$_4$ and evaporated in vacuo to dryness. Chromatography over silica gel and elution with ethyl acetate-hexane mixtures afforded 0.223 g of the title compound as a yellow oil (62% of the theoretical yield).

$\nu_{max}$ (CDCl$_3$) = 1787 cm$^{-1}$.

δ(CDCl$_3$): 1.02, 1.10 (9H, 2s, (CH$_3$)$_3$), 3.17–3.78 (4H, m, SCH$_2$, 3H), 3.82 (3H, s, OCH$_3$), 5.10 (1H, dd, J$_{trans}$1.5 Hz J$_{cis}$ 3 Hz, 4—H), 5.28–5.55 (4H, m, CH$_2$=, CO$_2$CH$_2$), 5.60–6.30 (1H, m, CH=), 6.78–8.30 (8H, m,

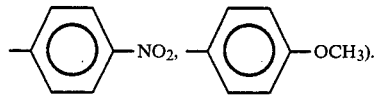

EXAMPLE 22

4-Nitrobenzyl 2-(4-allylsulphinylacetidin-2-on-1-yl)-3-(4-methoxyphenoxy)-3-thioxo-propionate To a stirred solution of 0.56 g of 4-nitrobenzyl 2-(4-allylsulphinylazetidin-2-on-1-yl)-3-(4-methoxyphenoxy)-3-trimethylacetylthio-propenate in dioxan-water (9:1 v/v) at 25° C. was added 82 mg of imidazole. After 30 minutes at room temperature the mixture was partitioned between ethyl acetate and water. The organic layer was separated and washed with water, with aqueous citric acid, with water, with saturated sodium bicarbonate, and with brine, and was then dried over MgSO4, and evaporated in vacuo to dryness. The resulting yellow oil was not purified. (Yield 420 mg, 87%).

$v_{max}$ (CDCl3)=1789 cm$^{-1}$.

δ(CDCl3): 3.15–3.65 (4H, m, SCH2, 3H), 3.8 (3H, s, OCH3), 5.10–5.60 (6H, m, CH2=, CO2CH2, CHCO2, 4H), 5.62–6.20 (1H, m, CH=), 6.70–8.24 (8H, m,

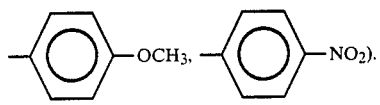

EXAMPLE 23

4-Nitrobenzyl 3-(4-methoxyphenoxy)-7-oxo-4-thia-1-azabicyclo[3.2.0-]hept-2-ene-2-carboxylate A mixture of 422 mg of 4-nitrobenzyl 2-(4-allylsulphinylazetidin-2-on-1-yl)-3-(4-methoxyphenoxy)-3-thioxopropanate, 214 mg of triphenylphosphine, and dioxan was heated under an argon atmosphere at 100° for 15 minutes. Then, the mixture was evaporated in vacuo to dryness, and the resulting oil was chromatographed on silica gel. Elution with ethyl acetate-hexane mixtures afforded 60 mg of the title compound (22% of the theoretical yield).

$v_{max}$(CDCl3)=1795 cm$^{-1}$. δ(CDCl3): 3.30–4.00 (4H, m, OCH3 and 6—H), 5.40 (2H, m, OCH2), d5.70 (1H, 2d, J$_{trans}$1.5 Hz, J$_{cis}$ 3 Hz, 5—H), 6.85–8.35 (8H, m,

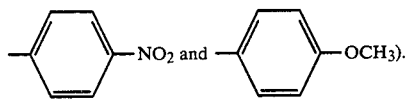

EXAMPLE 24

Sodium 3-(4-methoxyphenoxy)-7-oxo-4-thia-1-azabicyclo[3.2.0-]hept-2-ene-2-carboxylate A mixture of a solution of 60 mg of 4-nitrobenzyl 3-(4-methoxyphenoxy)-7-oxo-4-thia-1-azabicyclo[3,2,0-]hept-2-ene-2-carboxylate in dioxan and 15 mg of sodium bicarbonate in water, and 10% palladium/charcoal was hydrogenated at 50 psi at 25° for 60 minutes.

Then, the mixture was filtered through Celite, and lyophilised to yield 44 mg of the title compound as a pale yellow crystalline solid (99% of the theoretical yield).

EXAMPLE 25

4-Nitrobenzyl 2-(4-allylthioazetidin-2-on-1-yl)-3-(4-fluorophenoxy)-3-trimethylacetylthiopropenate To a stirred solution of 5.0 g of 4-nitrobenzyl 2-(4-allylthioazetidin-2-on-1-yl)-acetate in dry THF at −78° under argon was added a solution of a mixture of 7.0 ml hexamethyldisilazane and 33.4 mmol of n-butyllithium in dry THF. The mixture was stirred for 30 minutes, and a solution of 2.2 ml of p-fluorophenyl chlorothionoformate in 10 ml of dry THF was added. The mixture was warmed to −40°, and after 30 minutes was then cooled to −78°, and a solution of 2.3 ml of pivaloyl chloride in 20 ml of dry THF was added. The mixture was warmed to room temperature and, after 30 mins., the mixture was evaporated in vacuo to dryness. The resulting oil was partitioned between ethyl acetate and water, the organic layer was separated and washed with water, with aqueous citric acid, with saturated sodium bicarbonate, with brine, and was then dried over MgSO4 and evaporated to dryness. Chromatography over silica gel, eluting with hexane-ethyl acetate mixtures afforded the title compound (7.2 g, 84%) as a yellow oil.

$v_{max}$ (CDCl3)=1767 cm$^{-1}$.

δ(CDCl3): 1.02, 1.07 (9H, 2s, (CH3)3), 2.7–3.6 (4H, m, —SCH2, 3—H), 5.00 (1H, dd, J$_{trans}$1.5 Hz, J$_{cis}$ 3 Hz, 4—H), 5.10–5.30 (4H, m, CH2=, CO2OH2), 5.5–6.0 (1H, m, CH=), 6.8–8.2 (8H, m,

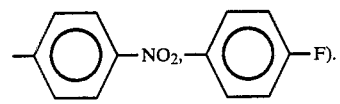

EXAMPLE 26

4-Nitrobenzyl 2-(4-allylsulphinylazetidin-2-on-1-yl)-3-(4-fluorophenoxy)-3-trimethylacetylthiopropenate To a solution of 4.0 g of 4-nitrobenzyl 2-(4-allylthioazetidin-2-on-1-yl)-3-(4-fluorophenoxy)-3-trimethylacetylthio-propenate in ethyl acetate at −78° was added a solution of 1.5 g of 80% m-chloroperoxybenzoic acid in ethyl acetate over 10 minutes. The reaction mixture was washed with saturated sodium bicarbonate solution, dried over MgSO4, and evaporated in vacuo to dryness. Chromatography over silica gel and elution with ethyl acetate-hexane mixtures afforded 2.4 g of the title compound as a yellow oil (58% of the theoretical yield).

$v_{max}$ (CDCl3)=1783 cm$^{-1}$.

δ(CDCl3): 1.01, 1.07 (9H, 2s, (CH3)3), 3.10, 3.70 (4H, m, SCH2, 3H), 5.10 (1H, dd, J$_{trans}$1.5 Hz, J$_{cis}$ 3 Hz, 4H), 5.20–5.40 (4H, m, CH2=, CO2CH2), 5.50–6.00 (1H, m, CH=), 6.80–8.20 (8H, m,

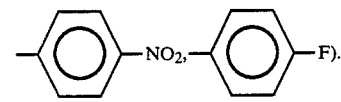

EXAMPLE 27

4-Nitrobenzyl 2-(4-allylsulphinylazetidin-2-on-1-yl)-3-(4-fluorophenoxy)-3-thioxo-propenate To a stirred solution of 0.83 g of 4-nitrobenzyl 2-(4-allylsulphinylazetidin-2-on-1-yl)-3-(4-fluorophenoxy)-3-trimethylacetylthio-propenate in dioxan-water (9:1 v/v) at room temperature was added 125 mg of imidazole. After 30 minutes at room temperature the mixture was partitioned between ethyl acetate and water. The organic layer was separated and washed with water, with aqueous citric acid, with water, with saturated sodium bicarbonate, and with brine, and was then dried over MgSO$_4$, and evaporated in vacuo to dryness to afford the title compound as a yellow oil (710 mg, 98%). This product was not purified further.

$\nu_{max}$ (CDCl$_3$) = 1791 cm$^{-1}$.

$\delta$(CDCl$_3$): 3.20–3.75 (4H, m, SCH$_2$, 3H), 5.10–5.50 (6H, m, CH$_2$=, CO$_2$CH$_2$, CHCO$_2$, 4H), 5.52–6.20 (1H, m, CH=), 6.80–8.30 (8H, m,

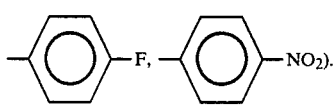

EXAMPLE 28

4-Nitrobenzyl 3-(4-fluorophenoxy)-7-oxo-4-thia-1-azabicyclo[3,2,0-]hept-2-ene-2-carboxylate A mixture of 1.15 g of 4-nitrobenzyl 2-(4-allylsulphinylazetidin-2-on-1-yl)-3-(4-fluorophenoxy)-3-thioxo-propanate, 600 mg of triphenylphosphine, and dioxan was heated under an argon atmosphere at 100° for 15 minutes. Then, the mixture was evaporated in vacuo to dryness, and the resulting oil was chromatographed on silica gel. Elution with ethyl acetate-hexane mixtures afforded 116 mg of the title compound (12% of the theoretical yield).

$\nu_{max}$ (CDCl$_3$) = 1798 cm$^{-1}$.

$\delta$(CDCl$_3$): 3.45 (1H, 2d, J$_{trans}$1.5 Hz, J$_{gem}$ 16 Hz, 6—H), 3.85 (1H, 2d, J$_{cis}$ 3 Hz, J$_{gem}$ 16 Hz, 6—H), 5.35 (2H, m, OCH$_2$), 5.60 (1H, 2d, J$_{trans}$1.5 Hz, J$_{cis}$ 3 Hz, 5-H), 6.90–8.20 (8H, m,

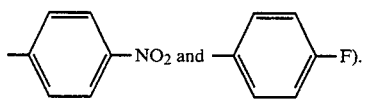

EXAMPLE 29

Sodium 3-(4-fluorophenoxy)-7-oxo-4-thia-1-azabicyclo[3,2,0-]hept-2-ene-2-carboxylate A mixture of a solution of 500 mg of 4-nitrobenzyl 3-(4-fluorophenoxy)-4-thia-1-azabicyclo[3,2,0]hept-2-ene-2-carboxylate in dioxan and 101 mg of sodium bicarbonate in water, and 10% palladium/charcoal was hydrogenated at 50 psi at 25° for 60 minutes. Then the reaction mixture was filtered through Celite, and then lyophilised to yield 348 mg of the title compound as a pale yellow crystalline solid (95% of the theoretical yield).

EXAMPLE 30

4-Nitrobenzyl 2-(4-chloroazetidin-2-on-1-yl)-3-(4-fluorophenoxy)-3-trimethylacetylthio-propenate To a solution of 7.2 g of 4-nitrobenzyl 2-(4-allylthioazetidin-2-on-1-yl)-3-(4-fluorophenoxy)-3-trimethylacetylthio-propenate (prepared as described in Example 25) in dichloromethane at −20°, was added a solution of 25 mmol of chlorine in carbon tetrachloride. After 30 minutes the mixture was warmed to room temperature, evaporated in vacuo, and the residual oil was chromatographed over silica gel. Elution with hexane-ethyl acetate mixtures afforded 4.6 g of the title compound as a pale yellow foam (67% of the theoretical yield).

$\nu_{max}$ (CDCl$_3$) = 1791 cm$^{-1}$.

$\delta$(CDCl$_3$): 1.03, 1.08 (9H, 2s, C(CH$_3$)$_3$), 3.26 (1H, 2d, J$_{trans}$1.5 Hz, J$_{3\alpha,3\beta}$16 Hz, 3$\beta$—H), 3.7 (1H, 2d, J$_{cis}$ 3 Hz, J$_{3\beta,3\alpha}$16 Hz, 3$\alpha$—H), 5.30 (2H, s, CO$_2$CH$_2$), 5.82–6.10 (1H, m, 4—H), 6.85–8.20 (8H, m,

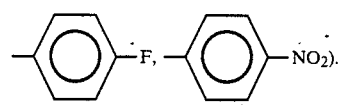

EXAMPLE 31

4-Nitrobenzyl 3-(4-fluorophenoxy)-7-oxo-4-thia-1-azabicyclo[3,2,0-]hept-2-ene-2-carboxylate To a stirred solution of 2.25 g of 4-nitrobenzyl 2-(4-chloroazetidin-2-on-1-yl)-3-(4-fluorophenoxy)-3-trimethylacetylthio-propenate in dioxan-water (9:1 v/v) at 5° C. was added 314 mg of imidazole. After 30 minutes at 5° C. the mixture was warmed to room temperature, and was partitioned between ethyl acetate and water. The organic layer was separated, and washed with water, with aqueous citric acid, with water, with saturated sodium bicarbonate, and with brine, and was then dried over MgSO$_4$, and evaporated in vacuo to dryness. Chromatography over silica gel and elution with ethyl acetate-hexane mixtures afforded 1.1 g of the title compound (63% of the theoretical yield) as a yellow foam.

This compound can be converted to the corresponding sodium salt as described in Example 29.

$\nu_{max}$ (CDCl$_3$) = 1798 cm$^{-1}$.

$\delta$(CDCl$_3$): 3.45 (1H, 2d, J$_{trans}$1.5 Hz, J$_{6\alpha,6\beta}$16 Hz, 6—H), 3.85 (1H, 2d, J$_{cis}$ 3 Hz, J$_{6\beta,6\alpha}$16 Hz, 6—H), 5.35 (2H, q, CO$_2$CH$_2$—), 5.60 (1H, dd, J$_{trans}$1.5 Hz, J$_{cis}$ 3 Hz, 5—H), 6.90–8.20 (8H, m,

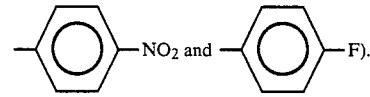

EXAMPLE 32

4-Nitrobenzyl 2-(allylthioazetidin-2-on-1-yl)-3-(4-chlorophenoxy)-3-trimethylacetylthiopropenate To a stirred solution of 15 g of 4-nitrobenzyl 2-(4-allylthioazetidin-2-on-1-yl)-acetate in dry THF at −78° under argon was added a solution of a mixture of 21 ml of hexamethyldisilazane and 62.7 mmol of n-butyllithium in dry THF. The mixture was stirred for 30 minutes, and a solution of 10 g of 4-chlorophenyl chlorothionoformate in 20 ml of dry THF was added. The mixture was warmed to −40° C. and after 30 minutes was then cooled to −78°, and a solution of 8.2 ml of pivaloyl chloride in dry THF was added. The mixture was warmed to room temperature, and after 30 minutes, the mixture was evaporated in vacuo to dryness. The resulting oil was partitioned between ethyl acetate and water, the organic layer was separated, and washed with water, with aqueous citric acid, with saturated sodium bicarbonate, with brine, and was then dried over MgSO$_4$ and evaporated to dryness.

EXAMPLE 33

4-Nitrobenzyl 2-(4-chloroazetidin-2-on-1-yl)-3-(4-chlorophenoxy)-3-trimethylacetylthio-propenate To a solution of 0.5 g of 4-nitrobenzyl 2-(4-allylthioazetidin-2-on-1-yl)-3-(4-chlorophenoxy)-3-trimethylacetylthio-propenate in dichloromethane at −20° C. was added a solution of 1.7 mmol chlorine in carbon tetrachloride. After 30 minutes the mixture was warmed to room temperature, evaporated in vacuo, and the residual oil was chromatographed over silica gel. Elution with hexane-ethyl acetate mixtures afforded 0.3 g of the title compound as a pale yellow foam (65% of the theoretical yield).

$v_{max}$ (CDCl$_3$)=1788 cm$^{-1}$.

$\delta$(CDCl$_3$): 1.08, 1.13 (9H, 2s. C(CH$_3$)$_3$), 3.1–3.9 (2H, m, 3—H), 5.38 (2H, s, CO$_2$CH$_2$), 5.9–6.15 (1H, m, 4—H), 6.90–8.32 (8H, m,

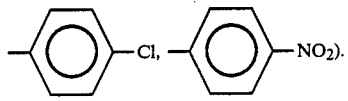

Chromatography over silica gel, eluting with hexane-ethyl acetate mixtures afforded the title compound (13.9 g, 53%) as a yellow oil.

$v_{max}$ (CDCl$_3$)=1770 cm$^{-1}$.

$\delta$(CDCl$_3$): 1.00, 1.07, (9H, 2s, (CH$_3$)$_3$), 2.78–3.60 (4H, m, S—CH$_2$, 3—H), 4.90 (1H, dd, J$_{trans}$ 1.5 Hz, J$_{cis}$ 3 Hz, 4—H), 5.05–5.32 (4H, m, CH$_2$, CO$_2$CH$_2$), 5.43–6.10 (1H, m, CH=), 6.7–8.1 (8H, m,

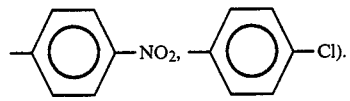

EXAMPLE 34

4-Nitrobenzyl 3-(4-chlorophenoxy)-7-oxo-4-thia-1-azabicyclo[3,2,0-]hept-2-ene-2-carboxylate To a stirred solution of 3.1 g of 4-nitrobenzyl 2-(4-chloroazetidin-2-on-1-yl)-3-(4-chlorophenoxy)-3-trimethylacetylthio-propenate in dioxan-water (9:1 v/v) at 5° was added 420 mg of imidazole. After 30 minutes at 5° C. the mixture was warmed to room temperature, was partitioned between ethyl acetate and water. The organic layer was separated, and was washed with water, with aqueous citric acid, with water, with saturated sodium bicarbonate, and with brine, and was then dried over MgSO$_4$, and evaporated in vacuo to dryness.

Chromatography over silica gel and elution with ethyl acetate-hexane mixtures afforded 1.0 g of the title compound (44%) as a yellow foam.

$v_{max}$ (CDCl$_3$)=1800 cm$^{-1}$.

$\delta$(CDCl$_3$): 3.50 (1H, 2d, J$_{trans}$ 1.5 Hz, J$_{gem}$ 16 Hz, 6—H), 3.95 (1H, 2d, J$_{cis}$ 3 Hz, J$_{gem}$ 16 Hz, 6—H), 5.35 (2H, m, CO$_2$CH$_2$), 5.70 (1H, dd, J$_{trans}$ 1.5 Hz, J$_{cis}$ 3 Hz, 5—H), 6.90–8.20 (8H, m,

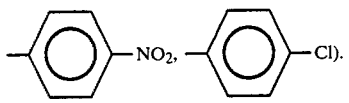

EXAMPLE 35

Sodium 3-(4-chlorophenoxy)-7-oxo-4-thia-1-azabicyclo[3,2,0-]hept-2-ene-2-carboxylate A mixture of a solution of 500 mg of 4-nitrobenzyl 3-(4-chlorophenoxy)-4-thia-1-azabicyclo[3,2,0]hept-2-ene-2-carboxylate in dioxan and 97 mg of sodium bicarbonate in water, and 10% palladium/charcoal was hydrogenated at 50 psi at 25° for 60 minutes.

Then, the mixture was filtered through Celite, and then lyophilised to yield 275 mg of the title compound as a pale yellow crystalline solid (72%).

EXAMPLE 36

4-Nitrobenzyl 2-(4-allylthioazetidin-2-on-1-yl)-3-(3-trifluoromethylphenoxy)-3-trimethylacetylthiopropenate To a stirred solution of 5.05 g of 4-nitrobenzyl 2-(4-allylthioazetidin-2-on-1-yl)-acetate in 100 ml of dry THF at −78° under argon was added a solution of a mixture of 7.0 ml of hexamethyldisilazane and 33.4 mmol of n-butyllithium in 40 ml of dry THF. The mixture was stirred for 5 minutes, and a solution of 4.52 g 3-trifluoromethylphenyl chlorothionoformate in dry THF was added. The mixture was warmed to −35° C.; and after 5 minutes was then cooled to −78°, and a solution of 2.75 ml of pivaloyl chloride in 15 ml of dry THF was added. The mixture was warmed to room temperature and, after 30 minutes, the mixture was evaporated in vacuo to dryness. The resulting oil was partitioned between ethyl acetate and water, the organic layer was separated, and washed with water, with aqueous citric acid, with saturated sodium bicarbonate, with brine, was dried over MgSO$_4$ and then evaporated to dryness. Chromatography over silica gel, eluting with hexane-ethyl acetate mixtures afforded the title compound (4.9 g, 52%) as a yellow oil.

$v_{max}$ (CDCl$_3$)=1762 cm$^{-1}$.

EXAMPLE 37

4-Nitrobenzyl 2-(4-chloroazetidin-2-on-1-yl)-3-(3-trifluoromethylphenoxy)-3-trimethylacetylthio-propenate To a solution of 4.9 g of 4-nitrobenzyl 2-(4-allylthiazetidin-2-on-1-yl)-3-(3-trifluoromethylphenoxy)-3-trimethylacetylthiopropenate in dichloromethane at −20°, was added a solution of 19.6 mmol of chlorine in carbon tetrachloride. After 30 minutes the mixture was warmed to room temperature, evaporated in vacuo, and the residual oil chromatographed over silica gel. Elution with hexane-ethyl acetate mixtures afforded 3.55 g of the title compound as a pale yellow foam (73% of the theoretical yield).

$\nu_{max}$ (CDCl$_3$) = 1791 cm$^{-1}$.

δ(CDCl$_3$): 1.05 (9H, s, C(CH$_3$)$_3$), 3.28 (1H, 2d, J$_{trans}$ 1.8 Hz, J$_{gem}$ 16 Hz), 3.73 (1H, 2d, J$_{cis}$ 3.6 Hz, J$_{gem}$ 16 Hz), 5.38 (2H, s, OCH$_2$), 6.08 (1H, 2d, J$_{trans}$ 1.8 Hz, J$_{cis}$ 3.6 Hz, 4—H), 7.0–8.3 (8H, m,

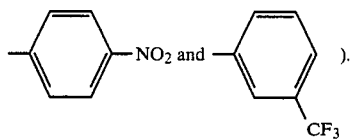

EXAMPLE 38

4-Nitrobenzyl 7-oxo-3-(3-trifluoromethyl)phenoxy)-4-thia-1-azabicyclo[3,2,0]hept-2-ene-2-carboxylate To a stirred solution of 3.5 g of 4-nitrobenzyl 2-(4-chloroazetidin-2-on-1-yl)-3-(3-trifluoromethylphenoxy)-3-trimethylacetylthio-propenate in dioxan-water (9:1 v/v) at 5° was added 730 mg of imidazole. After 30 minutes at 5° the mixture was warmed to room temperature, and was then partitioned between ethyl acetate and water. The organic layer was separated, and washed with water, with aqueous citric acid, with water, with saturated sodium bicarbonate, and with brine, and was then dried over MgSO$_4$, and evaporated in vacuo to dryness. Chromatography over silica gel and elution with ethyl acetate-hexane mixtures afforded 2250 mg of the title compound (85% of the theoretical yield) as a yellow foam.

$\nu_{max}$ (CDCl$_3$) = 1798 cm$^{-1}$.

δ(CDCl$_3$): 3.43 (1H, 2d, J$_{cis}$ 1.5 Hz, J$_{gem}$ 16 Hz, 6—H), 3.88 (1H, 2d, J$_{trans}$ 3 Hz, J$_{gem}$ 16 Hz, 6—H), 5.27 (2H, d+d, J$_{gem}$ 14 Hz, OCH$_2$), 5.68 (1H, 2d, J$_{cis}$ 1.5 Hz, J$_{trans}$ 3 Hz, 5—H), 7.5 (4H, m, —C$_6$H$_4$CF$_3$), 7.4–8.3 (4H, m —C$_6$H$_4$NO$_2$).

EXAMPLE 39

Sodium 7-oxo-3-(3-trifluoromethylphenoxy)-4-thia-1-azabicyclo[3,2,0]hept-2-ene-2-carboxylate A mixture of a solution of 602 mg of 4-nitrobenzyl 7-oxo-3-(3-trifluoromethylphenoxy)-4-thia-1-azabicyclo[3,2,0]hept-2-ene-2-carboxylate in dioxan and 108 mg sodium bicarbonate in water, and 10% palladium/charcoal was hydrogenated at 50 psi at 25° for 60 minutes.

Then, the mixture was filtered through Celite (Trade Mark) and lyophilised to yield 470 mg of the title compound as a pale yellow crystalline solid.

EXAMPLE 40

4-Nitrobenzyl 2-(4-allylthioazetidin-2-on-1-yl)-3-(1-naphthyloxy)-3-trimethylacetylthiopropenate To a stirred solution of 5.0 g of 4-nitrobenzyl 2-(4-allylthioazetidin-2-on-1-yl)acetate in dry THF at —78° under argon was added a solution of a mixture of 7.0 ml of hexamethyldisilazane and 33 mmol of n-butyllithium in dry THF. The mixture was stirred for 30 minutes, and a solution of 3.68 g of 1-naphthyloxy chlorothionoformate in 10 ml dry THF was added. The mixture was warmed to —40°, and after 30 minutes was then cooled to —78°, and 2.75 ml of trimethylacetyl chloride was added. The mixture was warmed to room temperature and, after 30 minutes, the mixture was evaporated in vacuo to dryness. The resulting oil was partitioned between ethyl acetate and water, the organic layer was washed with water, with aqueous citric acid, with saturated sodium bicarbonate, with brine, was dried over MgSO$_4$, and then evaporated to dryness. Chromatography over silica gel, eluting with hexane-ethyl acetate mixtures afforded the title compound (7.1 g, 77%) as a yellow oil.

δ(CDCl$_3$): 0.91, 0.99 (9H, 2s, C(CH$_3$)$_3$), 2.80–3.73 (4H, m, S—CH$_2$, 3—H), 5.02 (1H, m, 4—H); 5.07–5.47 (4H, m, CO$_2$CH$_2$, CH$_2$=), 5.53–6.16 (1H, m, CH=), 6.88–8.24 (11H, m,

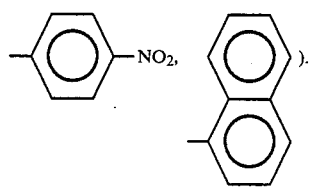

EXAMPLE 41

4-Nitrobenzyl 2-(4-chloroazetidin-2-on-1-yl)-3-(1-naphthyloxy)-3-trimethylacetylthiopropenate To a solution of 7.1 g of 4-nitrobenzyl 2-(4-allylthioazetidin-2-on-1-yl)-3-(1-naphthyloxy)-3-trimethylacetylthiopropenate in dichloromethane at —20° was added a solution of 23 mmol of chlorine in carbon tetrachloride. After 30 minutes the mixture was warmed to room temperature, evaporated in vacuo, and the residual oil was chromatographed over silica gel. Elution with hexane-ethyl acetate mixtures afforded 4.898 g of the title compound as a pale yellow foam (75% of the theoretical yield).

$\nu_{max}$ (CHCl$_3$) = 1790 cm$^{-1}$.

δ(CDCl$_3$): 0.91, 1.00 (9H, 2s, C(CH$_3$)$_3$), 3.25 (1H, 2d, J$_{3\alpha,3\beta}$ 16 Hz, J$_{trans}$ 1.5 Hz, 3—H), 3.70 (1H, 2d, J$_{3\alpha,3\beta}$ 16 Hz, J$_{cis}$ 3 Hz, 3—H), 5.22 (2H, s, CO$_2$CH$_2$), 6.00 (1H, dd, J$_{trans}$ 1.5 Hz, J$_{cis}$ 3 Hz, 4—H), 6.84–8.25 (11H, m,

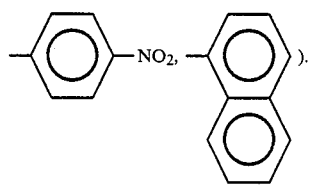

EXAMPLE 42

4-Nitrobenzyl 3-(1-naphthyloxy)-7-oxo-4-thia-1-azabicyclo[3,2,0]hept-2-ene-2-carboxylate To a stirred solution of 2.306 g of 4-nitrobenzyl 2-(4-chloroazetidin-2-on-1-yl)-3-(1-naphthyloxy)-3-trimethylacetylthiopropenate in dioxan-water (9:1 v/v) at 5° was added 469 g of imidazole. After 30 minutes at 5° the mixture was warmed to room temperature, and then partitioned between ethyl acetate and water. The organic layer was separated, was washed with water, with aqueous citric acid, with water, with saturated sodium bicarbonate, and with brine, was dried over MgSO4, and then evaporated in vacuo to dryness. Chromatography over silica gel and elution with ethyl acetate-hexane mixtures afforded 1.2684 g of the title compound (70%) as a yellow foam.

$\nu_{max}$ (CHCl3)=1800 cm$^{-1}$.

δ(CDCl3): 3.42 (1H, 2d, $J_{6\alpha,6\beta}$ 16 Hz, $J_{trans}$ 1.5 Hz, 6—H), 3.88 (1H, 2d, $J_{6\alpha,6\beta}$ 16 Hz, $J_{cis}$ 3 Hz, 6—H), 5.34 (2H, q, CO2CH2), 5.61 (1H, dd, $J_{trans}$ 1.5 Hz, $J_{cis}$ 3 Hz, 5—H), 7.11–8.24 (11H, m,

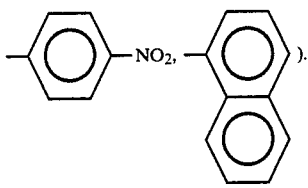

m/e molecular ion at 448.0800.

EXAMPLE 43

Sodium 3-(1-naphthyloxy)-7-oxo-4-thia-1-azabicyclo[3,2,0]hept-2-ene-2-carboxylate A mixture of a solution of 800 mg of 4-nitrobenzyl 3-(1-naphthyloxy)-7-oxo-4-thia-1-azabicyclo[3,2,0]hept-2-ene-2-carboxylate in dioxan and 150 mg of sodium bicarbonate in water, and 10% palladium/charcoal was hydrogenated at 50 psi at 25° for 60 minutes.

Then, the mixture was filtered through Celite, and lyophilized to yield 490 mg of the title compound as a pale yellow crystalline solid (82%).

EXAMPLE 44

4-Nitrobenzyl 2-(4-allylthioazetidin-2-on-1-yl)-3-(4-methylthiophenoxy)-3-trimethylacetylthiopropenate To a stirred solution of 5 g of 4-nitrobenzyl 2-(4-allylthioazetidin-2-on-1-yl)-acetate in 100 ml of dry THF at −78° under argon was added a solution of a mixture of 6.93 ml of hexamethyldisilazane and 33 mmol of n-butyllithium in 50 ml of dry THF.

The mixture was stirred for 5 minutes, and a solution of 3.28 g of 4-methylthio-phenyl chlorothionoformate in 10 ml of dry THF was added. The mixture was warmed to −40°, and after 30 minutes was then cooled to −78°, and a solution of 2.75 ml of pivaloyl chloride in dry THF was added. The mixture was warmed to room temperature, and after 30 minutes, the mixture was evaporated in vacuo to dryness. The resulting oil was partitioned between ethyl acetate and water, the organic layer was separated, was washed with water, with aqueous citric acid, with saturated sodium bicarbonate, with brine, was dried over MgSO4, and then evaporated to dryness. Chromatography over silica gel, eluting with hexane-ethyl acetate mixtures afforded the title compound (5.14 g) as a yellow oil. (57% of the theoretical yield).

$\nu_{max}$ (CHCl3)=1768, 1776 (sh) cm$^{-1}$.

δ(CDCl3): 1.05, 1.10 (9H, 2s, C(CH3)3), 2.49 (3H, s, S—CH3), 2.80–3.55 (4H, m, S—CH2—, 3—H), 5.02 (1H, dd, $J_{trans}$ 1.5 Hz, $J_{cis}$ 3 Hz, 4—H), 5.18–5.50 (2H, m, CH2=), 5.57–6.03 (1H, m, CH=), 6.90–8.40 (8H, m,

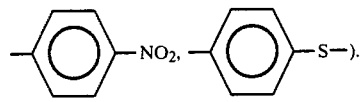

m/e base peak 57.0726 C(CH3)3.

EXAMPLE 45

4-Nitrobenzyl 2-(4-chloroazetidin-2-on-1-yl)-3-(4-methylthiophenoxy)-3-trimethylacetylthiopropenate To a solution of 2.28 g of 4-nitrobenzyl 2-(4-allylthioazetidin-2-on-1-yl)-3-(4-methylthiophenoxy)-3-trimethylacetylthiopropenate in dichloromethane at −20°, was added solution of 7.6 mmol of chlorine in carbon tetrachloride. After 30 minutes the mixture was warmed to room temperature, evaporated in vacuo, and the residual oil was chromatographed over silica gel. Elution with hexane-ethyl acetate mixtures afforded 1.48 g of the title compound as a yellow foam (69% of the theoretical yield).

$\nu_{max}$ (CHCl3)=1788 cm$^{-1}$.

δ (CDCl3): 1.05, 1.09 (9H, 2s, C(CH3)3), 2.46 (3H, s, S—CH3), 3.23 (1H, 2d, $J_{trans}$1.5 Hz, $J_{3\alpha,3\beta}$16 Hz, 3β—H), 3.63 (1H, 2d, $J_{cis}$3 Hz, $J_{3\beta,3\alpha}$16Hz, 3α—H), 5.31 (2H, s, CO2—CH2—), 5.78, 5.99 (1H, 2dd, $J_{trans}$1.5 Hz, J cis 3 Hz, 4—H), 6.77 ∝ 8.20 (8H, m,

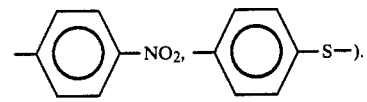

m/e base peak 57.0726 C(CH3)3.

EXAMPLE 46

4-Nitrobenzyl 3-(4-methylthiophenoxy)-7-oxo-4-thia-1-azabicyclo[3,2,0]hept-2-2-carboxylate To a stirred solution of 0.28 g of 4-nitrobenzyl 2-(4-chloroazetidin-2-on-1-yl)-3-(4-methylthiophenoxy)-3-trimethylacetylthiopropenate in dioxan-water (9:1 v/v) at 5° was added 70 mg of imidazole. After 30 minutes at 5° the mixture was warmed to room temperature, and was partitioned between ethyl acetate and water. The organic layer separated, was washed with water, with aqueous citric acid, with water with saturated sodium bicarbonate, and with brine, was dried over MgSO4, and was evaporated in vacuo to dryness. Chromatography over silica gel and elution with ethyl acetate-hexane mixtures afforded 155 mg of the title compound (70%) as a yellow oil.

$\nu_{max}$ (CHCl3)=1800 cm$^{-1}$.

δ (CDCl3): 2.49 (3H, s, S—CH3), 3.47 (1H, 2d, $J_{trans}$1.5 Hz, $J_{gem}$16 Hz, 6—H), 3.91 (1H, 2d, $J_{cis}$3 Hz, $J_{gem}$16 Hz, 6—H), 5.36 (2H, q, CO2—CH2—), 5.67 (1H, dd, $J_{trans}$1.5H $J_{cis}$3 Hz, 5—H), 6.98–8.23 (8H, m,

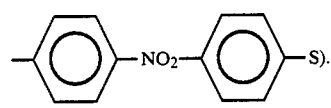

m/e molecular ion 444.0.

EXAMPLE 47

Sodium 3-(4-methylthiophenoxy)-7-oxo-4-thia-1-azabicyclo[3,2,0]hept-2-ene-2-carboxylate A mixture of a solution of 70 mg of 4-nitrobenzyl 3-(4-methylthiophenoxy)-7-oxo-4-thia-1-azabicyclo[3,2,0]hept-2-ene-2-carboxylate in dioxan and 13 mg of sodium bicarbonate in water, and 10% palladium/-charcoal was hydrogenated at 50 psi at 35° for 60 minutes.

Then, the mixture was filtered through Celite, and lyophilized to yield 58 mg of the title compound as a pale yellow crystalline solid (111%).

EXAMPLE 48

4-Nitrobenzyl 2-(4-allylthioazetidin-2-on-1-yl)-3-(4-methylsulphinylphenyloxy)-3-trimethylacetylthiopropenate To a solution of 1.275 g of 4-nitrobenzyl 2-(4-allylthioazetidin-2-on-1-yl)-3-(4-methylthiophenoxy)-3-trimethylacetylthiopropenate (prepared as described in Example 44) in ethyl acetate at $-78°$ was added a solution of 0.451 g of 81% m-chloroperoxybenzoic acid in ethyl acetate over 10 minutes. The reaction mixture was washed with saturated sodium bicarbonate solution, dried over MgSO4 and evaporated in vacuo to dryness. Chromatography over silica gel and elution with ethyl acetate-hexane mixtures afforded 0.488 g of the title compound as a yellow oil (38% of the theoretical yield).

$v_{max}$ (CHCl$_3$)=1770 cm$^{-1}$.

δ (CDCl$_3$): 1.06, 1.11 (9H, 2s, C(CH$_3$)$_3$), 2.67 (3H, s, S—CH$_3$), 3.00–3.60 (4H, m, S—CH$_2$, 3—H), 4.92 (1H, dd, J$_{trans}$1.5 Hz, J$_{cis}$3 Hz, 4—H), 5.02–5.35 (2H, m, CH=), 5.38–6.03 (1H, m, CH=), 6.94–8.15 (8H, m,

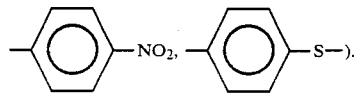

EXAMPLE 49

4-Nitrobenzyl 2-(4-chloroazetidin-2-on-1-yl)-3-(4-methylsulphinylphenoxy)-3-trimethylacetylthiopropenate To a solution of 0.488 g of 4-nitrobenzyl 2-(4-allylthioazetidin-2-on-1-yl)-3-(4-methylsulphinylphenoxy)-3-trimethylacetylthiopropenate in dichloromethane at $-20°$, was added dropwise a solution of 1.58 mmol of chlorine in carbon tetrachloride. After 30 minutes the mixture was warmed to room temperature, evaporated in vacuo, and the residual oil was chromatographed over silica gel. Elution with hexane-ethyl acetate mixtures afforded 0.24 g of the title compound as a pale yellow foam (53% of the theoretical yield).

$v_{max}$ (CHCl$_3$)=1790 cm$^{-1}$.

δ (CDCl$_3$): 1.05, 1.11 (9H, 2s, C(CH$_3$)$_3$), 2.69 (3H, s, S—CH$_3$), 3.21 (1H, 2d, J$_{trans}$1.5 Hz, J$_{3\alpha,3\beta}$16 Hz, 3β—H), 3.65 (1H, 2d, J$_{cis}$3 Hz, J$_{3\beta,3\alpha}$16 Hz, 3α—H), 5.25 (2H, s, CO$_2$CH$_2$), 5.91 (1H, dd, J$_{trans}$1.5 Hz, J$_{cis}$3 Hz, 4—H), 6.91–8.18 (8H, m,

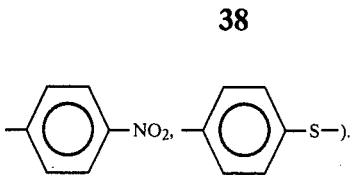

m/e base peak 57.0720, C(CH$_3$)$_3$.

EXAMPLE 50

4-Nitrobenzyl 2-(4-chloroazetidin-2-on-1-yl)-3-(4-methylsulphinylphenoxy)-3-trimethylacetylthiopropenate To a solution of 0.536 g of 4-nitrobenzyl 2-(4-chloroazetidin-2-on-1-yl)-3-(4-methylthiophenoxy)-3-trimethylacetylthiopropenate (prepared as described in Example 46) in ethyl acetate at $-20°$ was added a solution of 0.2 g of 81% m-chloroperoxybenzoic acid in ethyl acetate over 10 minutes. The reaction mixture was washed with saturated sodium bicarbonate solution, dried over MgSO4, and evaporated in vacuo to dryness. Chromatography over silica gel and elution with ethyl acetate-hexane mixtures afforded 0.5 g of title compound as a yellow oil (27% of the theoretical yield).

$v_{max}$ (CHCl$_3$)=1790 cm$^{-1}$.

δ (CDCl$_3$): 1.05, 1.11 (9H, 2s, C(CH$_3$)$_3$), 2.69 (3H, s, S—CH$_3$), 3.21 (1H, 2d, J$_{trans}$1.5 Hz, J$_{3\alpha,3\beta}$16 Hz, 3β—H), 3.65 (1H, 2d, J$_{cis}$3 Hz, J$_{3\beta,3\alpha}$16 Hz, 3α—H), 5.25 (2H, s, CO$_2$CH$_2$), 5.91 (1H, dd, J$_{trans}$1.5 Hz, J$_{cis}$3 Hz, 4—H), 6.91–8.18 (8H, m,

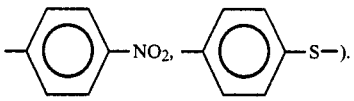

m/e base peak 57.0720, C(CH$_3$)$_3$.

EXAMPLE 51

4-Nitroenzyl 3-(4-methylsulphinylphenoxy)-7-oxo-4-thia-1-azabicyclo[3,2,0]hept-2-ene-2-carboxylate To a stirred solution of 0.24 g of 4-nitrobenzyl 2-(4-chloroazetidin-2-on-1-yl)-3-(4-methylsulphinylphenoxy)-3-trimethylacetylthiopropenate (prepared as described in Example 49 or Example 50) in dioxan-water (9:1 v/v) at 5° was added 56 mg of imidazole. After 30 minutes at $-5°$ the mixture was warmed to room temperature, and was partitioned between ethyl acetate and water, the organic layer was spearated, was washed with water, with aqueous citric acid, with water, with saturated sodium bicarbonate, and with brine, was dried over MgSO4, and then evaporated in vacuo to dryness. Chromatography over silica gel and elution with ethyl acetate-hexane mixtures afforded 70 mg of the title compound (37%) as a yellow oil.

$v_{max}$ (CHCl$_3$)=1802 cm$^{-1}$.

δ (CDCl$_3$): 2.72 (3H, s, S—CH$_3$), 3.46 (1H, 3d, J$_{trans}$1.5 Hz, J$_{gem}$16 Hz, 6—H), 3.88 (1H, 2d, J$_{cis}$3 Hz, J$_{gem}$16 Hz, 6—H), 5.22 (2H, q, CO$_2$—CH$_2$—), 5.64 (1H, dd, J$_{trans}$1.5 Hz, J$_{cis}$3Hz, 5—H), 7.06–8.11 (8H, m,

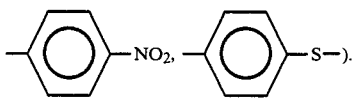

EXAMPLE 52

Sodium 3-(4-methylsulphinylphenoxy)-7-oxo-4-thia-1-azabicyclo[3,2,0]hept-2-ene-2-carboxylate A mixture of a solution of 70 mg of 4-nitrobenzyl 3-(4-methylsulphinylphenoxy)-7-oxo-4-thia-1-azabicyclo[3,2,0]hept-2-ene-2-carboxylate in dioxan and 13 mg of sodium bicarbonate in water, and 10% palladium/charcoal was hydrogenated at 50 psi at 25° for 60 minutes. Then, the mixture was filtered through Gelite, and lyophilized to yield 58 mg of the title compound as a pale yellow crystalline solid.

We claim:

1. A penem derivative of the formula I

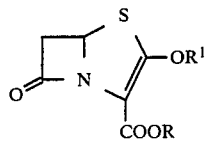

in which

R is hydrogen or a carboxyl esterifying group $R^1$ is phenyl or naphthyl, each which is unsubstituted or substituted by one, two or three substituents, which may be the same or different, selected from the group consisting of halogen, cycloalkyl having from 5 to 10 carbon atoms —$NH_2$, —$CONH_2$, —$NO_2$, —CN, —$R^2$, —$OR^2$, —$SR^2$, —SO—$R^2$, —$SO_2R^2$, —CO—$R^2$, —CO—O—$R^2$, —$CH_2$—CO—O—$R^2$, —$NHR^2$, —$NR^2R^{2'}$, —CO—NH—$R^2$, —CO—$NR^2R^{2'}$, —NH—CO—$R^2$, —NH—CO—$NH_2$, —NH—CO—NH—$R^2$, —NH—$SO_2$—$R^2$, —$CF_3$, —CO—OH, —$CH_2$—CO—OH, wherein $R^2$ and $R^{2'}$ are the same or different and each represents alkyl of 1 to 4 carbon atoms or a physiologically acceptable salt thereof.

2. A compound as claimed in claim 1 wherein $R^1$ is phenyl which unsubstituted or substituted by —SO—$R^2$ or —$SO_2$—$R^2$.

3. A compound as claimed in claim 2 wherein $R^2$ is methyl.

4. A compound as claimed in claim 1 wherein $R^1$ is phenyl which is substituted by fluorine.

5. A compound as claimed in claim 1 wherein $R^1$ is phenyl which is substituted by chlorine.

6. A compound as claimed in claim 1 wherein $R^1$ is phenyl which is substituted by cyano.

7. A compound as claimed in claim 1 wherein $R^1$ is phenyl which is substituted by acetyl.

8. A compound as claimed in claim 1 wherein $R^1$ is phenyl which is substituted by methoxycarbonyl.

9. An antibacterial pharmaceutical preparation which comprises an effective amount of a compound as claimed in claim 1 together with a pharmaceutically suitable carrier.

10. A method for combating bacterial infection in a host which comprises orally or parenterally administering to said host a compound as claimed in claim 1.

11. A compound as claimed in claim 1 wherein R is hydrogen or a carboxyl esterifying group removable by hydrolysis, by photolysis, by reduction or by enzyme action to give the free acid.

12. The compound as claimed in claim 1, wherein $R^1$ is phenyl, or phenyl substituted by fluorine, chlorine, —$SOCH_3$ is —$SO_2CH_3$.

13. The compound as claimed in claim 1, wherein $R^1$ is phenyl which is unsubstituted or substituted by —SO—$R^2$, $SO_2$—$R^2$, fluorine or chlorine.

14. The compound as claimed in claim 1, wherein $R^1$ is an unsubstituted or substituted naphthyl.

* * * * *